United States Patent
Seto et al.

(10) Patent No.: US 8,506,584 B2
(45) Date of Patent: Aug. 13, 2013

(54) FLUID JET DEVICE, DRIVE DEVICE OF FLUID JET DEVICE, SURGICAL INSTRUMENT, AND METHOD OF DRIVING FLUID JET DEVICE

(75) Inventors: Takeshi Seto, Chofu (JP); Shinichi Miyazaki, Suwa (JP); Kunio Tabata, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 853 days.

(21) Appl. No.: 12/552,768

(22) Filed: Sep. 2, 2009

(65) Prior Publication Data

US 2010/0069937 A1  Mar. 18, 2010

(30) Foreign Application Priority Data

Sep. 16, 2008  (JP) .................................. 2008-236106

(51) Int. Cl.
*A61B 17/32* (2006.01)
*F16K 31/02* (2006.01)
*H01L 41/00* (2006.01)

(52) U.S. Cl.
USPC ....... 606/167; 251/129.06; 251/333; 310/314

(58) Field of Classification Search
USPC ............... 606/167, 169, 106, 159, 1; 604/22, 604/19; 83/53, 177; 137/561 R, 1, 164.13; 251/129.06, 129.08, 333; 310/314, 317
See application file for complete search history.

(56) References Cited

U.S. PATENT DOCUMENTS

| | | | |
|---|---|---|---|
| 7,420,807 B2 | 9/2008 | Mikubo et al. | |
| 2008/0086077 A1* | 4/2008 | Seto et al. ....................... | 604/48 |
| 2008/0110600 A1 | 5/2008 | Mikubo et al. | |
| 2009/0043480 A1 | 2/2009 | Seto et al. | |

FOREIGN PATENT DOCUMENTS

| | | |
|---|---|---|
| JP | A-2006-242176 | 9/2006 |
| JP | A-2007-205189 | 8/2007 |
| JP | A-2008-82202 | 4/2008 |
| JP | A-2009-39384 | 2/2009 |

* cited by examiner

*Primary Examiner* — Elizabeth Houston
(74) *Attorney, Agent, or Firm* — Oliff & Berridge, PLC

(57) ABSTRACT

A fluid jet device including a fluid chamber with variable capacity and a capacity varying section adapted to vary the capacity of the fluid chamber in response to supply of a drive signal. A drive waveform section making the capacity varying section operate so as to compress the capacity of the fluid chamber and a restoring drive waveform section making the capacity varying section operate to restore the capacity of the fluid chamber before compressing the capacity in a signal waveform. The drive signal supply section controls supply content of the drive signal to provide a restoring period adapted to restore a steady state of the fluid flowing toward an inside of the fluid chamber in a period from when the compressing drive waveform section in the drive signal is supplied to when a subsequent compressing drive waveform section is supplied.

14 Claims, 11 Drawing Sheets

| ADDRESS | TIME | VOLTAGE |
|---------|------|---------|
| 101 | t0 | P0 |
| 102 | t1 | P1 |
| 103 | t2 | P2 |
| 104 | t3 | P3 |
| 105 | t4 | P4 |
| ⋮ | ⋮ | ⋮ |

FLUID JET DEVICE, DRIVE DEVICE OF FLUID JET DEVICE, SURGICAL INSTRUMENT, AND METHOD OF DRIVING FLUID JET DEVICE

Japanese Patent Application No. 2008-236106 filed on Sep. 16, 2008, is hereby incorporated by reference in its entirety.

BACKGROUND

1. Technical Field

The present invention relates to a fluid jet device for emitting a jet of a fluid at high speed, and in particular to a fluid jet device suitable for emitting a jet of a fluid in the condition of maintaining desired jet force.

2. Related Art

In the past, as a fluid jet device for incising or excising body tissue, there is known a device provided with a pulsation generation section having a fluid chamber with a variable capacity, an entrance channel and exit channel communicated to the fluid chamber, and a capacity varying section for varying the capacity of the fluid camber in response to supply of a drive signal, a connection channel having one end communicated to the exit channel and the other end provided with a fluid jet opening section (a nozzle) with a diameter smaller than that of the exit channel, a connection channel tube provided with the connection channel penetrating therethrough and having rigidity with which the pulsation of the fluid flowing from the fluid chamber can be transmitted to the fluid jet opening section, and a pressure generation section for supplying the entrance channel with the fluid, and for supplying the entrance channel with the fluid with the pressure generation section at a constant pressure, and at the same time varying the capacity of the fluid chamber with the capacity varying section to generate the pulsation, thereby performing ejection operation of the fluid (e.g., JP-A-2008-82202 (Document 1)).

According to the Document 1, a patent application by the inventors of the invention, in the case in which the capacity of the fluid chamber of a fluid jet device is not varied, the fluid flows through the fluid chamber in the condition in which the supply pressure by the pressure generation section (e.g., a pump) and the channel resistance balanced with each other. When shrinking the fluid chamber rapidly, the pressure in the fluid chamber rises. At that moment, since an increased amount of fluid ejected from the exit channel is larger than a decreased amount of flow volume of the fluid flowing from the entrance channel into the fluid chamber, a pulsation flow occurs in the connection channel. The pressure pulsation in the ejection operation propagates in the connection channel tube, and thus the fluid jet is emitted from the fluid jet opening section of the nozzle at the tip of the connection channel tube. The fluid chamber becomes in a vacuum state (0 atm or nearly 0 atm) immediately after the pressure rise due to the interaction between decrease in inflow volume of the fluid from the entrance channel and increase in outflow of the fluid from the exit channel. As a result, after predetermined time has elapsed due to both of the pressure of the pump and the vacuum state inside the fluid chamber, there is restored the flow of the fluid in the entrance channel towards the inside of the fluid chamber at the same speed as before the operation of the piezoelectric element.

In the technology of the related art described in the Document 1, although it is arranged that the capacity varying section configured including the piezoelectric element and a diaphragm is driven by a pulsed drive signal, in the case, for example, in which it is driven by a simple sinusoidal drive signal, the subsequent capacity reduction operation (compressing operation) might be performed before the flow proceeding toward the inside of the fluid chamber is restored to the steady state. If the subsequent compressing operation is performed before restoring the steady state, it is not achievable to obtain sufficiently strong jet force (jet).

SUMMARY

An advantage of some aspects of the invention is to provide a fluid jet device, a drive device for the fluid jet device, a surgical instrument, and a driving method of the fluid jet device, each suitable for continuously emitting jet of the pulsation flow in the condition of maintaining desired jet force.

A first aspect of the invention is directed to a fluid jet device including a fluid chamber with a variable capacity, an entrance channel communicated with the fluid chamber, an exit channel communicated with the fluid chamber, a capacity varying section adapted to vary the capacity of the fluid chamber in response to supply of a drive signal, an opening section communicated with a different end of the exit channel from an end of the exit channel with which the exit channel is communicated with the fluid chamber, a pressure generation section adapted to supply the entrance channel with a fluid, and a drive signal supply section adapted to supply the capacity varying section with a drive signal including a compressing drive waveform section making the capacity varying section operate so as to compress the capacity of the fluid chamber and a restoring drive waveform section making the capacity varying section operate so as to restore the capacity of the fluid chamber before compressing the capacity in a signal waveform of one cycle, and the drive signal supply section controls supply content of the drive signal so as to provide a restoring period adapted to restore a steady state of the fluid flowing toward an inside of the fluid chamber in a period from when the compressing drive waveform section in the drive signal is supplied to the capacity varying section to when a subsequent one of the compressing drive waveform section is supplied to the capacity varying section.

According to the configuration described above, when the drive signal supply section supplies the capacity varying section with the compressing drive waveform section in the drive signal, the capacity varying section acts to compress the capacity of the fluid chamber, and thus the inside of the fluid chamber is compressed. Then, when the supply of the compressing drive waveform section is terminated, the restoring drive waveform section in the drive signal is then supplied to the capacity varying section. Thus, the capacity varying section acts in the direction of restoring the capacity of the fluid chamber to the state prior to the compression, thereby restoring the inside of the fluid chamber, which is now in the compressed state. Further, the drive signal supply section controls the supply content of the drive signal so that the restoring period for restoring the flow of the fluid toward the fluid chamber to be in the steady state is provided in a period from the end of supply of the compressing drive waveform section to the supply of the subsequent compressing drive waveform section.

In other words, when the drive signal supply section terminates the supply of the previous compressing drive waveform section to the capacity varying section, it is possible to restore the steady state (the state in which the fluid is flowing while the supply pressure from the pressure generation section and the flow resistance are balanced with each other) in the fluid chamber prior to the supply of the subsequent compressing drive waveform section.

Thus, since it becomes possible to make the capacity varying section perform the subsequent compressing operation after the flow of the fluid toward the fluid chamber is restored to be the steady state, it is possible to obtain an advantage that emission of the fluid jet can continuously be performed while keeping the jet force in a constant and strong state.

Here, the expression "to be communicated with" means that one thing and the other thing are connected to each other, no matter whether directly or indirectly, so that a fluid can flow therethrough. For example, the condition in which an end of the exit channel and the fluid jet opening section are connected to each other directly or via a channel tube or the like so that the fluid can flow therethrough corresponds to the expression.

Further, a second aspect of the invention is directed to the fluid jet device of the first aspect of the invention, wherein a time length of the compressing drive waveform section is denoted as $T_{red}$, a time length of the restoring drive waveform section is denoted as $T_{exp}$, average pressure in the fluid chamber in a supply period of the compressing drive waveform section is denoted as $P_{gen}$, pressure applied to the entrance channel in the fluid chamber on a pressure generation section side in a supply period of the restoring drive waveform section is denoted as $P_{sup}$, and the drive signal supply section supplies the capacity varying section with the drive signal configured including the compressing drive waveform section with the time length $T_{red}$ and the restoring drive waveform section with the time length $T_{exp}$ satisfying a relationship of a following formula.

$$T_{red} \times (P_{gen} - P_{sup}) \leq T_{exp} \times P_{sup}$$

Here, denoting the cross section of the entrance channel as s, the momentum $M_g$ acting on the entrance channel on the fluid chamber side is expressed as $M_g = s \times T_{red} \times (P_{gen} - P_{sup})$, and the momentum $M_s$ acting on the entrance channel on the pressure generation section side is expressed as $M_s = s \times T_{exp} \times P_{sup}$. Further, in general, $P_{sup}$ takes a far smaller value compared to $P_{gen}$ ($P_{gen} \gg P_{sup}$).

Further, in a period (the period of $T_{exp}$) during which the capacity of the fluid chamber is expanding (restoring the original capacity), the average pressure of the fluid chamber becomes 0 atm or nearly 0 atm because the fluid is drawn due to the inertance of the exit channel. In other words, if the momentum $M_s$ provided thereto in $T_{exp}$ is equal to or larger than the momentum $M_g$ provided thereto in $T_{red}$, the fluid can be restored to the original steady state.

Therefore, in the case of the configuration described above, since it is possible to supply the capacity varying section with the drive signal having the compressing drive waveform section with the time length $T_{red}$ and the restoring drive waveform section with the time length $T_{exp}$ satisfying the relationship of the formula described above, the fluid can be restored from the vacuum state to the original steady state in one cycle period of the drive signal.

Thus, since it becomes possible to make the capacity varying section perform the subsequent compressing operation after the flow of the fluid toward the fluid chamber is restored to be the steady state, it is possible to obtain an advantage that emission of the fluid jet can continuously be performed while keeping the jet force in a strong state.

Further, it might be possible, for example, that a signal is raised rapidly and then dropped rapidly as the burst waveform shown in FIG. 16, and then, waiting for the flow toward the fluid chamber to be restored before supplying the subsequent signal.

However, in this case, since the inside of the fluid chamber expands (restores the original capacity) rapidly, the vacuum bubbles in the fluid chamber also expand, and the gases solved in the fluid become apt to be discharged toward the vacuum bubbles. As a result, although the flow to the fluid chamber is restored and the vacuum bubbles disappear, since the bubbles caused by the gases once discharged from the liquid never disappear, the bubbles lower the rigidity of the fluid chamber, and as a result, the rise in pressure might be prevented to make the emission of the fluid jet weaker.

According to the configuration described above, since the drive signal satisfying the relationship of the formula described above can be supplied to the capacity varying section, $P_{gen} \gg P_{sup}$ is satisfied, and therefore, $T_{exp}$ becomes a longer time length than $T_{red}$, and as a result, the capacity of the fluid chamber thus compressed is restored to the original state relatively slowly, and as a result, the vacuum bubbles become smaller, and it becomes possible to make it difficult to discharge the gases from the fluid to the vacuum bubbles.

Thus, the advantage that the rigidity of the fluid chamber can be prevented from dropping due to the bubbles of the gases can also be obtained.

Further, a third aspect of the invention is directed to the fluid jet device of the first or the second aspect of the invention, wherein the drive signal supply section controls the supply content of the drive signal so as to provide the restoring period in the supply period of the restoring drive waveform section.

According to the configuration described above, in a period of one cycle of the drive signal, it is possible to perform compression of the capacity of the fluid chamber, restoring to the original capacity, and restoring of the flow of the fluid toward the fluid chamber to the steady state. Thus, since it becomes possible to make the capacity varying section perform the subsequent compressing operation after the flow of the fluid toward the fluid chamber is restored to be the steady state, it is possible to obtain an advantage that emission of the fluid jet can continuously be performed while keeping the jet force in a strong state.

Further, a fourth aspect of the invention is directed to the fluid jet device of the third aspect of the invention, wherein the drive signal supply section supplies the capacity varying section with the drive signal having a constant waveform section holding a constant signal level as the restoring period between the compressing drive waveform section and the restoring drive waveform section and in a part of the restoring drive waveform section.

According to the configuration described above, it is possible to operate the capacity varying section so as to keep (stop varying the capacity) the capacity of the fluid chamber constant for a predetermined time period after compressing the capacity of the fluid chamber as a restoring period.

Thus, since the vacuum bubbles can be made to disappear in the state in which the capacity is compressed and the capacity is not substantially varied, an advantage of making the vacuum bubbles disappear in a short period of time can be obtained.

Further, since it is also possible to restore the capacity after the vacuum bubbles disappear or roughly disappear, an advantage that the discharge of the gases from the fluid can be prevented can also be obtained.

Further, a fifth aspect of the invention is directed to either one of the fluid jet device of the first through fourth aspects of the invention, wherein a storage section adapted to store waveform information of the drive signal is additionally provided, the drive signal supply section generates the drive signal based on the waveform information stored in the waveform information storage section, and supplies the capacity varying section with the drive signal.

According to the configuration described above, for example, by storing the waveform data sampled at a predetermined cycle as the waveform information, it is possible to easily generate the drive signal of the target waveform from the waveform data.

Further, a sixth aspect of the invention is directed to the fluid jet device of either one of the first through fifth aspects of the invention, wherein the drive signal supply section supplies the capacity varying section with the drive signal having the signal waveform of one cycle configured by combining a part of a sine wave, which forms the compressing drive waveform section, and a time length of one cycle of which is T1, and a part of a sine wave, which forms the restoring drive waveform section, and a time length of one cycle of which is T2 (T1≠T2).

According to the configuration described above, since it is possible to configure the drive signal by combining a part of one sine wave and a part of another sine wave, the time length of one cycle of the one sine wave and the time length of one cycle of the another sine wave being different from each other, denoting, for example, the wavelength of the sine wave of T1 as λ1, the wavelength of the sine wave of T2 as λ2, the drive signal can be configured by combining a waveform portion corresponding to the anterior half λ1/2 of the sine wave of T1 and a waveform portion corresponding to the posterior half λ2/2 of the sine wave of T2.

Thus, there is obtained an advantage that the drive signal, which has the time length of the posterior half cycle longer then the time length of the anterior half cycle, and at the same time, which has the signal waveform of one cycle different from a simple sine wave, can easily be configured. In other words, the drive signal including the restoring period in the restoring drive waveform section can easily be configured.

Further, a seventh aspect of the invention is directed to the fluid jet device of the fifth aspect of the invention, wherein a shape of a trapezoidal wave is adopted as the signal waveform of one cycle.

According to the configuration described above, since the drive signal (analog signal) can be generated from the waveform data of a smaller number of samples compared to the case with the sine wave signals, the data capacity of the waveform data stored in the waveform information storage section can be reduced.

Thus, there can be obtained an advantage that the storage capacity of the waveform information storage section can be made smaller compared to the case of using the sine wave signal as the drive signal, and at the same time, there can also be obtained an advantage that a larger number of types of waveform data can be stored in the waveform information storage section with the same capacity compared to the case in which the sine wave signal is used as the drive signal.

Further, an eighth aspect of the invention is directed to the fluid jet device of the seventh aspect of the invention, wherein the storage section stores nodal point information of the trapezoidal wave as the waveform information, and the drive signal supply section generates the drive signal of the trapezoidal wave based on the nodal point information stored in the storage section.

According to the configuration described above, by storing only the nodal point information of each of the trapezoidal waves as the waveform information it is possible to generate the desired drive signal from the waveform information, and therefore, it is possible to reduce the waveform information to be stored in the storage section to a smaller amount of data.

Further, in the case in which real-time access is required to generate the drive signal, it is enough to read out a smaller amount of data compared to the case of using the sine wave signal as the drive signal, and therefore, such a high-speed access mechanism required for the case of using the sine wave signal as the drive signal is not required.

Therefore, there can be obtained an advantage that the drive control using the waveform information with various wavelengths and amplitudes can be realized at lower cost compared to the case of using the sine wave signal as the drive signal.

Further, a ninth aspect of the invention is directed to the fluid jet device of either one of the first through eighth aspects of the invention, wherein a diameter of an end of the exit channel on a fluid chamber side is set to be larger than a diameter of an end of the exit channel on an opening section side.

According to the configuration described above, there can be obtained an advantage that the fluid flowing from the fluid chamber side end of the exit channel can be emitted in the opening section side end of the exit channel as a pulsed droplet with higher pressure and higher speed.

Further, a tenth aspect of the invention is directed to the fluid jet device of either one of the first through ninth aspects of the invention, wherein an inertance of the entrance channel is set to be larger than an inertance of the exit channel.

According to the configuration described above, when driving the capacity varying section to compress the capacity of the fluid chamber, a larger pulsation flow than the inflow amount of the fluid from the entrance channel to the fluid chamber occurs in the exit channel, thus the pulsed fluid ejection can be performed in the connection channel tube.

Further, an eleventh aspect of the invention is directed to the fluid jet device of either one of the first through ninth aspects of the invention, wherein a combined inertance on an upstream side of the fluid chamber including the entrance channel is larger than an inertance on a downstream side of the fluid chamber including the exit channel.

According to the configuration described above, when driving the capacity varying section to compress the capacity of the fluid chamber, a larger pulsation flow than the inflow amount of the fluid from the entrance channel to the fluid chamber occurs in the exit channel, thus the pulsed fluid ejection can be performed in the connection channel tube.

Further, a twelfth aspect of the invention is directed to the fluid jet device of either one of the first through eleventh aspects of the invention, wherein there are further provided a connection channel having a first end communicated with the exit channel, and a second end provided with the opening section having a diameter smaller than a diameter of the exit channel, and a connection channel tube through which the connection channel penetrates, and which transmits pulsation of the fluid flowing from the fluid chamber to the opening section.

According to the configuration described above, it becomes possible to more strongly emit a jet of the fluid, and at the same time, in the case in which the fluid jet device according to this aspect of the invention is used, for example, as a surgical instrument, it becomes applicable to various operations such as an operation on the brain in which the affected area is located in a recess.

Further, a thirteenth aspect of the invention is directed to the fluid jet device of either one of the first through twelfth aspects of the invention, wherein the capacity varying section is configured including a diaphragm adapted to seal an end of the fluid chamber, and a piezoelectric element having one end fixed to the diaphragm and one of expanding and shrinking in a direction perpendicular to a seal surface in response to supply of the drive signal, and the drive signal supply section makes the piezoelectric element expand to deform the diaphragm toward an inside of the fluid chamber by supplying the compressing drive waveform section in the drive signal, and makes the piezoelectric element shrink to restore the diaphragm in a deformed state to the diaphragm in a state prior to the deformation by supplying the restoring drive waveform section in the drive signal.

According to the configuration described above, since the piezoelectric element is adopted as the capacity varying section, there can be obtained an advantage that the capacity variation of the fluid chamber can easily be controlled by the drive signal, and at the same time, there can also be obtained an advantage that the simplification of the structure and associated downsizing can be realized. Further, since it is possible to set the highest frequency of the capacity variation of the fluid chamber to be a high frequency equal to or higher than, for example, 1 kHz, there can be obtained an advantage that the emission of a jet of the pulsation flow can be executed at high speed and with a short cycle period.

Meanwhile, a fourteenth aspect of the invention is directed to a drive device of a fluid jet device including a fluid chamber with a variable capacity, an entrance channel and an exit channel each communicated with the fluid channel, a capacity varying section adapted to vary a capacity of the fluid chamber in response to supply of a drive signal, an opening section communicated with a different end of the exit channel from an end of the exit channel communicated with the fluid chamber, a pressure generation section adapted to supply the entrance channel with a fluid, and a drive signal supply section adapted to supply the capacity varying section with a drive signal including a compressing drive waveform section making the capacity varying section operate so as to compress the capacity of the fluid chamber and a restoring drive waveform section making the capacity varying section operate so as to restore the capacity of the fluid chamber before compressing the capacity in a signal waveform of one cycle, and the drive signal supply section controls supply content of the drive signal so as to provide a restoring period adapted to restore a steady state of the fluid flowing toward an inside of the fluid chamber in a period from when the compressing drive waveform section in the drive signal is supplied to the capacity varying section to when a subsequent one of the compressing drive waveform section is supplied to the capacity varying section.

According to the configuration described above, substantially the same functions and advantages as of the fluid jet device according to the first aspect of the invention can be obtained.

Further, a fifteenth aspect of the invention is directed to a surgical instrument adapted to assist a therapeutic treatment of an affected area by fluid jet emission, including the fluid jet device according to either one of the first through thirteenth aspects of the invention.

According to the configuration described above, it is possible to perform assistance of a therapeutic treatment such as excision of an affected area such as a tumor using a fluid jet emission by the fluid jet device according to either one of the first through thirteenth aspects of the invention.

Further, a sixteenth aspect of the invention is directed to a method of driving a fluid jet device including the steps of (a) providing a fluid chamber with a variable capacity, an entrance channel and an exit channel each communicated with the fluid chamber, a capacity varying section adapted to vary a capacity of the fluid chamber in response to supply of a drive signal, an opening section communicated with a different end of the exit channel from an end of the exit channel communicated with the fluid chamber, a pressure generation section adapted to supply the entrance channel with a fluid, and a drive signal supply section, and (b) making the drive signal supply section supply the capacity varying section with a drive signal including a compressing drive waveform section making the capacity varying section operate so as to compress the capacity of the fluid chamber and a restoring drive waveform section making the capacity varying section operate so as to restore the capacity of the fluid chamber before compressing the capacity in a signal waveform of one cycle, and in step (b), the drive signal supply section is made to control supply content of the drive signal so as to provide a restoring period adapted to restore a steady state of the fluid flowing toward an inside of the fluid chamber in a period from when the compressing drive waveform section in the drive signal is supplied to the capacity varying section to when a subsequent one of the compressing drive waveform section is supplied to the capacity varying section.

According to the configuration described above, substantially the same functions and advantages as of the fluid jet device according to the first aspect of the invention can be obtained.

BRIEF DESCRIPTION OF THE DRAWINGS

The invention will now be described with reference to the accompanying drawings, wherein like numbers reference like elements.

DESCRIPTION OF EXEMPLARY EMBODIMENTS

First Embodiment

A first embodiment of the invention will hereinafter be explained with reference to the accompanying drawings. FIGS. 1 through 8 are diagrams showing a fluid jet device, a drive device of the fluid jet device, a surgical instrument, and a method of driving the fluid jet device according to the first embodiment of the invention.

It should be noted that the fluid jet device according to the embodiment of the invention can be adopted for various purposes such as drawing with ink or the like, cleaning a fine object and a structure, ablation or excision of an object, and a surgical knife, and in the embodiment explained hereinafter, the explanations are presented exemplifying the fluid jet device suitable for incising or excising body tissue. Therefore, the fluid used in the embodiment is water, saline, medical solution, or the like.

Figure 1:
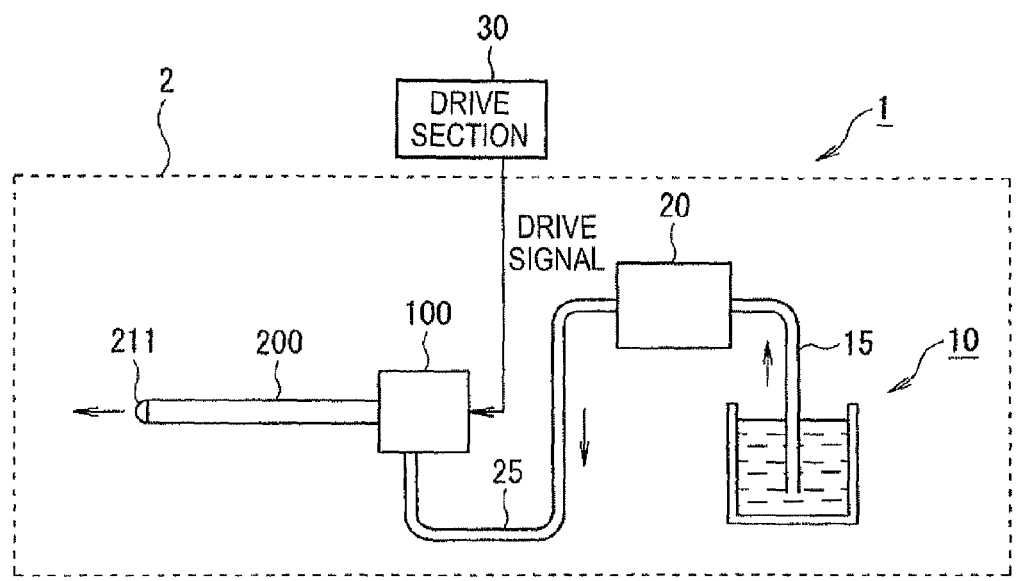
FIG. 1 is an explanatory diagram showing a schematic configuration of a fluid jet device according to the present embodiment of the invention.

Firstly, a configuration of the fluid jet device according to the embodiment of the invention will be explained with reference to FIG. 1. FIG. 1 is an explanatory diagram showing a schematic configuration of the fluid jet device 1 according to the present embodiment of the invention.

As shown in FIG. 1, the fluid jet device 1 is configured including, as a basic configuration, a fluid jet emitting section 2 configured including a fluid container 10 for containing the fluid, a pump 20 as a pressure generation section, and a pulsation generation section 100 for making a pulsing flow of the fluid supplied from the pump 20, and a drive section 30 for driving the pulsation generation section 100.

A connection channel tube 200 with a thin pipy shape is connected to the pulsation generation section 100, and a tip portion of the connection channel tube 200 is provided with a nozzle 211 with a shrunk channel inserted therein.

Then, the flow of the fluid in the fluid jet device 1 will briefly be explained with reference to FIGS. 1 and 2.

Figure 2:
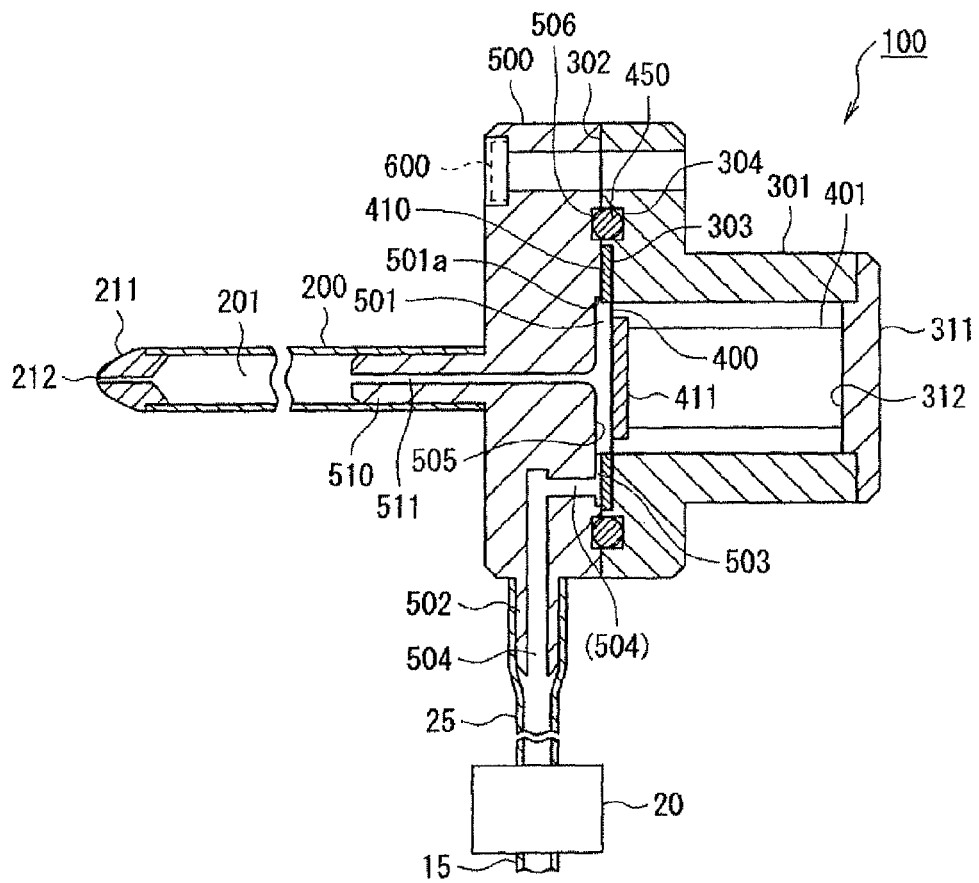
FIG. 2 is a cross-sectional view showing a structure of a pulsation generation section according to the embodiment of the invention.

Here, FIG. 2 is a cross-sectional view showing a structure of the pulsation generation section 100 according to the embodiment of the invention. It should be noted that the lateral direction in FIG. 2 corresponds to the vertical direction. Further, FIG. 2 is a cross-sectional diagram along the A-A' line shown in FIG. 3 described later.

The fluid contained in the fluid container 10 is suctioned by the pump 20 via a connection tube 15, and supplied to the pulsation generation section 100 at constant pressure via a connection tube 25. The pulsation generation section 100 is provided with a fluid chamber 501, and a capacity varying section for varying the capacity of the fluid chamber 501 in accordance with a drive signal from the drive section 30, and driving the capacity varying section to generate pulsation, thereby emitting a jet of fluid at high speed through a connection channel tube 200 and a nozzle 211. Detailed explanations of the pulsation generation section 100 will be described later.

It should be noted that, when performing an operation using the fluid jet device 1, the region the operator grips is the pulsation generation section 100. Therefore, it is preferable that the connection tube 25 to the pulsation generation section 100 is as flexible as possible. In order for achieving the above, it is preferable to apply the lowest possible pressure to the fluid in a range in which the fluid can be sent to the pulsation generation section 100 using a flexible tube with a thin wall.

Further, in particular in the case such as an operation on the brain, in which a failure in the device might cause a significant accident, it is necessary to prevent a high-pressure fluid from spouting in response to break of the connection tube 25, and in view of this point, it is required to keep the fluid at low pressure.

Hereinafter, a structure of the pulsation generation section 100 will be explained with reference to FIGS. 2 through 4.

Figure 3:
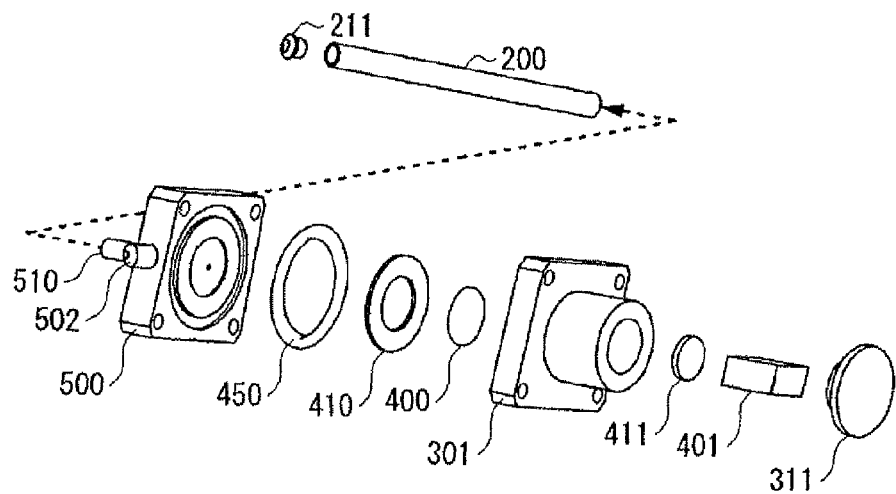
FIG. 3 is an exploded diagram of a fluid jet emitting section.
Figure 4:
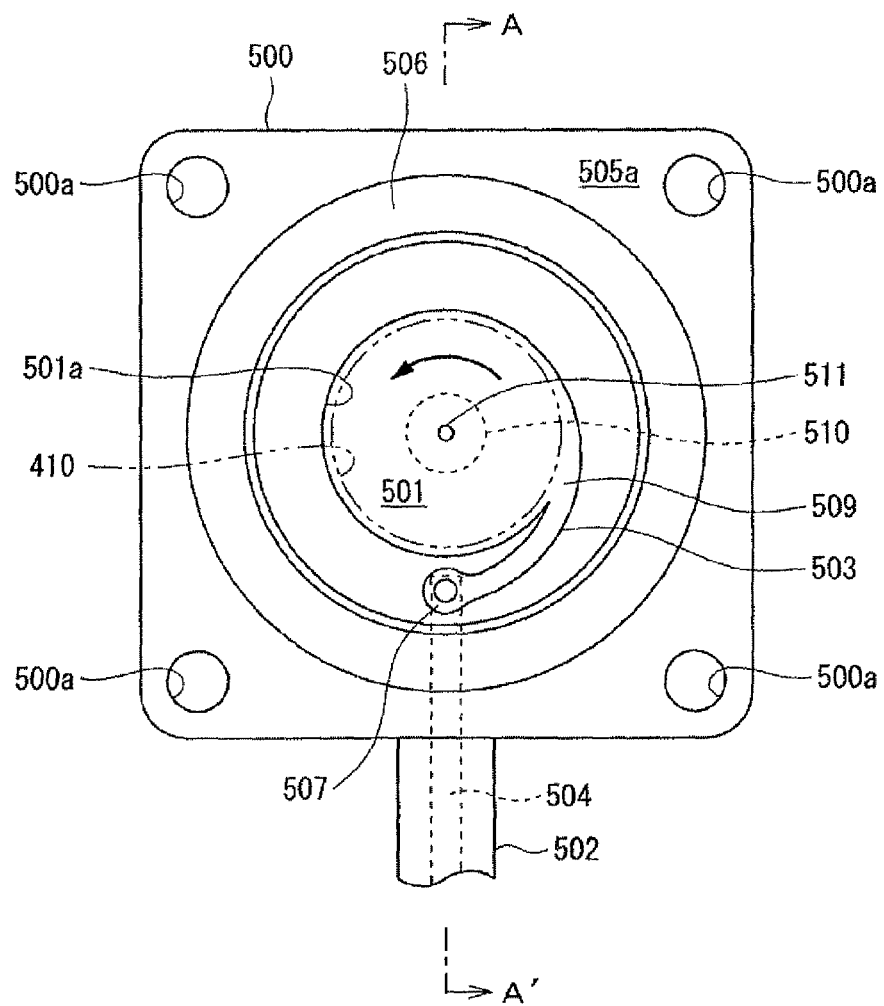
FIG. 4 is a plan view showing a form of an entrance channel.

Here, FIG. 3 is an exploded view of the fluid jet emitting section 2, and FIG. 4 is a plan view showing a form of an entrance channel 503, and shows an appearance of an upper case 500 viewed from a bonded surface side between the upper case 500 and a lower case 301.

As shown in FIGS. 2 through 4, the pulsation generation section 100 is provided with the upper case 500 with threaded holes 500a opened on the four corners thereof, and the lower case 301 with threaded holes 301a (not shown) opened on the four corners thereof. Further, the upper case 500 and the lower case 301 are bonded on the surfaces thereof opposed to each other so that the threaded holes 500a and the threaded holes 301a are opposed respectively to each other, and four screws 600 (not shown) are screwed in the threaded holes 500a and 301a, thereby screwing the upper case 500 and the lower case 301 to each other.

The lower case 301 is a hollow cylinder-shaped member having a brim section, and one end thereof is sealed with a bottom plate 311. In the internal space of the lower case 301, there is disposed a piezoelectric element 401 as one of the members forming the capacity varying section.

The piezoelectric element 401 is a stacked piezoelectric element, and forms an actuator. One end of the piezoelectric element 401 is fixed to a diaphragm 400 via an upper plate 411, and the other end thereof is fixed to an upper surface 312 of the bottom plate 311.

Further, the diaphragm 400 is formed of a disc-like metal thin plate, and has a peripheral portion adhering and fixed to a bottom surface of a ring-like concave section 303 provided to the upper surface side of the lower case 301 within the concave section 303. On the upper surface of the diaphragm 400, there is disposed, in a stacked manner, a reinforcing plate 410 formed of a disk-like metal thin plate having a circular opening section at the center thereof.

According to this configuration, by the drive section 30 inputting a drive signal to the piezoelectric element 401, the piezoelectric element 401 expands or shrinks, and the upward force caused by the expansion and the downward force caused by the shrinkage move the upper plate 411 in up-and-down directions. Then, the movement of the upper plate 411 deforms the diaphragm 400, thereby varying the capacity of the fluid chamber 501.

In other words, the capacity varying section is composed of the piezoelectric element 401, the upper plate 411, the diaphragm 400, and the reinforcing plate 410.

The upper case 500 has a circular concave section formed at the central section of the surface thereof opposed to the lower case 301, and a solid of revolution composed of the concave section and the diaphragm 400 and filled with a fluid is defined as the fluid chamber 501. In other words, the fluid chamber 501 is defined as a space surrounded by a seal surface 505 of the concave section of the upper case 500, inner circumferential wall 501a, and the diaphragm 400. At a substantially central section of the fluid chamber 501, there is bored an exit channel 511.

The exit channel 511 penetrates from the fluid chamber 501 to an end of an exit channel tube 510 disposed so as to protrude from one end surface of the upper case 500. A connection section of the exit channel 511 with the seal surface 505 of the fluid chamber 501 is smoothly rounded in order for reducing the fluid resistance.

It should be noted that although the shape of the fluid chamber 501 described hereinabove is a substantially cylindrical shape sealed at the both ends, this is not a limitation, but the shape can be a conical shape, a trapezoidal shape, or a hemispherical shape in the side view. For example, by adopting a funnel-like shape as the connection section of the exit channel 511 with the seal surface 505, it becomes easier to discharge bubbles in the fluid chamber 501 described later.

A connection channel tube 200 is connected to the exit channel tube 510. The connection channel tube 200 is provided with a connection channel 201 penetrating therethrough, and the diameter of the connection channel 201 is larger than the diameter of the exit channel 511. Further, the tube wall of the connection channel tube 200 is formed to have a thickness in a range of providing rigidity not absorbing the pressure pulsation of the fluid.

A nozzle 211 is inserted in the tip portion of the connection channel tube 200. The nozzle 211 is provided with a fluid jet opening section 212 penetrating therethrough. The diameter of the fluid jet opening section 212 is smaller than the diameter of the connection channel 201.

On a side surface of the upper case 500, there is disposed an entrance channel tube 502 so as to protrude therefrom, the entrance channel tube 502 being inserted into the connection tube 25 for supplying the fluid from the pump 20, and provided with an entrance channel side connection channel 504 penetrating therethrough. The connection channel 504 is communicated with the entrance channel 503. The entrance channel 503 is formed on the peripheral portion of the seal surface 505 of the fluid chamber 501 to have a groove shape, and is communicated with the fluid chamber 501.

On the bonded surface between the upper case 500 and the lower case 301 at a position apart from the outer circumference of the diaphragm 400, there are formed a gasket groove 304 on the lower case 301 side and a gasket groove 506 on the upper case 500 side, and in the space formed by the gasket grooves 304, 506, there is mounted a ring-like gasket 450.

Here, when assembling the upper case 500 and the lower case 301 together, a peripheral portion of the diaphragm 400 and a peripheral portion of the reinforcing plate 410 have close contact with each other by the peripheral portion of the seal surface 505 of the upper case 500 and the bottom surface of the concave section 303 of the lower case 301. On this occasion, the gasket 450 is pressurized by the upper case 500 and the lower case 301 to prevent leakage of the fluid from the fluid chamber 501.

The inside of the fluid chamber 501 becomes in a high-pressure state of, for example, 30 atm (3 MPa) or higher when ejecting the fluid, and although it is possible that the fluid slightly leaks at each of the bonding sections between the diaphragm 400, the reinforcing plate 410, the upper case 500, and the lower case 301, the gasket 450 prevents the leakage.

When disposing the gasket 450 as shown in FIG. 2, the gasket 450 is compressed by the pressure of the fluid leaking from the fluid chamber 501 at high pressure, and is further firmly pressed against inside walls of the gasket grooves 304, 506, and therefore, the leakage of the fluid can more reliably be prevented. Accordingly, the high-rate of pressure rise in the fluid chamber 501 can be maintained when driving.

Subsequently, the entrance channel 503 provided to the upper case 500 will be explained in greater detail.

As shown in FIG. 4, the entrance channel 503 is formed by a groove provided to the peripheral portion of the seal surface 505 of the upper case 500 and the reinforcing plate 410 pressed against and fixed to the seal surface 505.

The entrance channel 503 is communicated with the fluid chamber 501 at one end thereof, and is communicated with the connection channel 504 at the other end thereof. At a connection section between the entrance channel 503 and the connection channel 504, there is formed a fluid reservoir 507. Further, a connection section between the fluid reservoir 507 and the entrance channel 503 is smoothly rounded, thereby reducing the fluid resistance.

Further, the entrance channel 503 is communicated with the fluid chamber 501 toward a substantially tangential direction with respect to the inner circumferential sidewall 501a of the fluid chamber 501. The fluid supplied from the pump 20 at constant pressure flows along the inner circumferential sidewall 501a (in the direction indicated by the arrow in the drawing) to generate a swirling flow in the fluid chamber 501. Due to the centrifugal force of the swirling flow, the bubbles with a low density contained in the fluid chamber 501 are gathered at the central portion of the swirling flow.

Then, the bubbles thus gathered at the central portion are discharged from the exit channel 511. Therefore, it is more preferable for the exit channel 511 to be disposed near the center of the swirling flow, namely at the axially central portion of the solid of revolution. In the example shown in FIG. 4, the entrance channel 503 is curved to have a spiral planar shape. Although it is possible for the entrance channel 503 to be communicated with the fluid chamber 501 with a straight line, it is curved because it is required to increase the channel length of the entrance channel 503 in order for obtaining a desired inertance in a small space.

It should be noted that as shown in FIG. 2, the reinforcing plate 410 is disposed between the diaphragm 400 and the peripheral portion of the seal surface 505 where the entrance channel 503 is formed. The purpose for providing the reinforcing plate 410 is to enhance durability of the diaphragm 400. Since a notch-like connection opening section 509 is provided to the connection section of the entrance channel 503 with the fluid chamber 501, it is conceivable that stress concentration is caused in the vicinity of the connection opening section 509 when the diaphragm 400 is driven at a high frequency, thereby causing fatigue breakdown. Therefore, it is arranged that the stress concentration can be prevented from occurring in the diaphragm 400 by disposing the reinforcing plate 410 having a continuous opening section without a notch section.

Further, although in the fluid jet emitting section 2 explained hereinabove, it is arranged that the four threaded holes 500a are bored at outer peripheral portion of the upper case 500, and the upper case 500 and the lower case 301 are screwed at the threaded holes, the configuration of the fluid jet emitting section 2 is not limited thereto. For example, although omitted from the drawing, it is possible to bond the reinforcing plate 410 and the diaphragm 400 with each other, thereby stacking and fixing them integrally to each other. As a fixing method, it is possible to adopt sticking with an adhesive, solid-phase diffusion bonding, welding, and so on, and it is further preferable that the reinforcing plate 410 and the diaphragm 400 adhere to each other in the bonded surface.

Further, although in the fluid jet emitting section 2 described hereinabove, there is adopted a configuration of connecting the exit channel 511 and the nozzle 211 via the connection channel tube 200, the configuration is not limited thereto, and it is also possible to insert the nozzle 211 in an end of the exit channel 511 on the opposite side to the fluid chamber 501 without using the connection channel tube 200. On this occasion, a more simple configuration becomes possible.

Further, when used in an operation, it is more preferable to adopt a configuration of using the connection channel tube 200 to obtain a longer distance between a handpiece and a fluid jet ejection port.

Then, fluid ejection of the pulsation generation section 100 according to the present embodiment is performed by a difference between the inertance L1 (also referred to as a combined inertance L1 in some cases) on the entrance channel side and the inertance L2 (also referred to as a combined inertance L2 in some cases) on the exit channel side.

Firstly, the inertance will be explained.

The inertance L is expressed as L=ρ×h/S assuming that ρ denotes the density of the fluid, S denotes the cross section of the channel, and h denotes the length of the channel. When assuming that the pressure difference of the channel is ΔP, and the flow rate of the fluid flowing through the channel is Q, by transforming the motion equation in the channel using the inertance L, the relationship of ΔP=L×dQ/dt is derived.

In other words, the inertance L represents the degree of the influence exerted on the time variation of the flow rate, and the larger the inertance L is, the smaller the time variation of the flow rate is, and the smaller the inertance L is, the larger the time variation of the flow rate is.

Further, a combined inertance with respect to a parallel connection of a plurality of channels or a series connection of a plurality of channels with shapes different from each other can be calculated by combining the inertances of the respective channels in substantially the same manner as the parallel connection or the series connection of inductances in an electrical circuit.

It should be noted that regarding the inertance L1 on the entrance channel side, since the connection channel 504 is set to have a diameter sufficiently larger than that of the entrance channel 503, the inertance L1 can be obtained by calculating only the inertance of the entrance channel 503. Further, the connection tube for connecting the pump 20 and the entrance channel has flexibility, and therefore, is omitted from the calculation of the inertance L1.

Further, regarding the inertance L2 on the exit channel side, in the case in which the diameter of the connection channel 201 is far larger than that of the exit channel, and the thickness of the tube portion (tube wall) of the connection channel tube 200 is small, the influence on the inertance L2 is minimal. Therefore, the inertance L2 on the exit channel side can be replaced by the inertance of the exit channel 511.

In the case in which the thickness of the tube wall of the connection channel tube 200 is large, the inertance L2 is obtained as the combined inertance of the exit channel 511, the connection channel 201, and the nozzle 211.

Further, in the present embodiment, the channel length and the cross section of the entrance channel 503 and the channel length and the cross section of the exit channel 511 are set so that the inertance L1 on the entrance channel side becomes larger than the inertance L2 on the exit channel side.

Hereinafter, a detailed configuration of the drive section 30 will be explained with reference to FIGS. 5 through 7.

Figure 5:
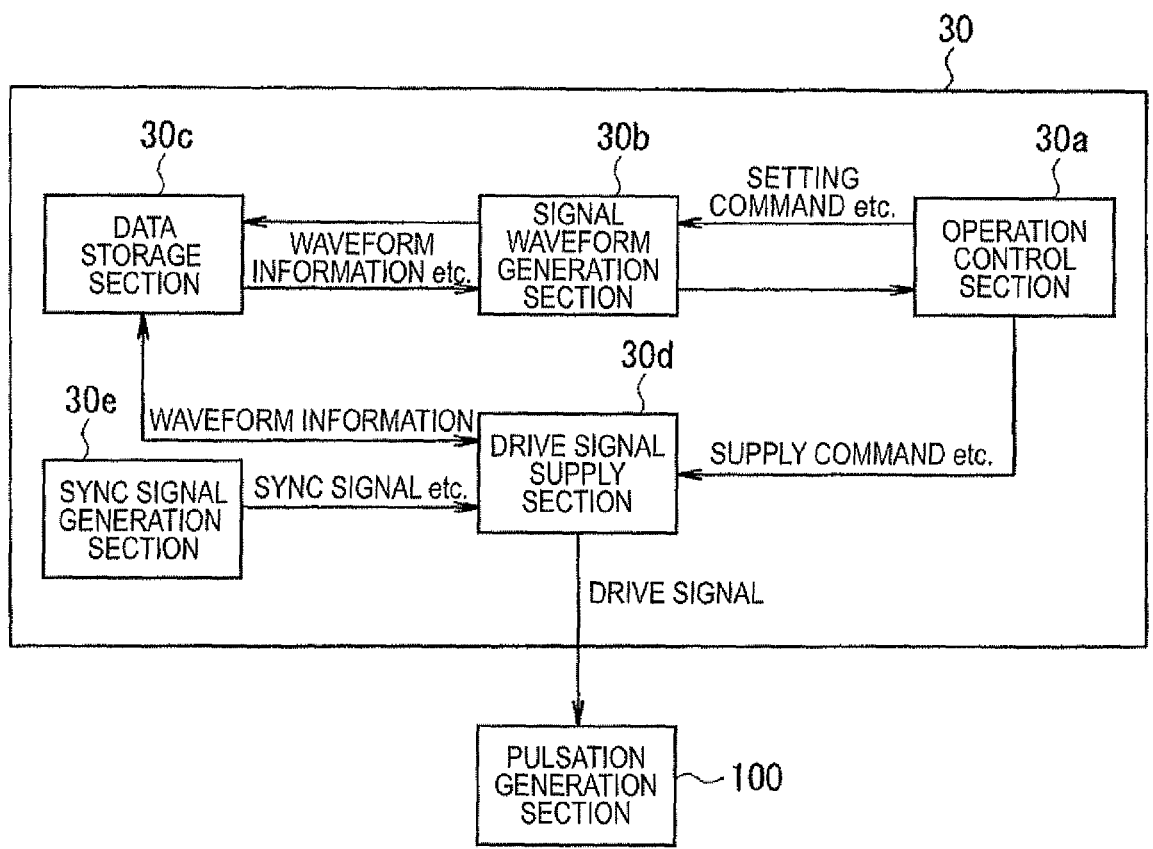
FIG. 5 is a block diagram showing a detailed configuration of a drive section.

Here, FIG. 5 is a block diagram showing a detailed configuration of the drive section 30. Further, FIG. 6 is a flowchart showing a process of generating a signal waveform in the drive section 30. Still further, FIG. 7 is a flowchart showing a process of supplying the pulsation generation section 100 with a drive signal in the drive section 30.

As shown in FIG. 5, the drive section 30 is configured including an operation control section 30a, a signal waveform generation section 30b, a data storage section 30c, a drive signal supply section 30d, and a sync signal generation section 30e.

The operation control section 30a assumes the role of providing each of the constituents with an operational instruction in accordance with an operational input from an input device (not shown) of the fluid jet device 1, and has a function of controlling various kinds of operational processes such as a process of generating the signal waveform, or a process of supplying the drive signal.

The signal waveform generation section 30b has a function of generating a signal waveform with a shape suitable for driving the pulsation generation section 100 using the waveform information, a data table, and measurement data stored in the data storage section 30c based on the jet emission intensity of the fluid jet emitting section 2, which is set based on the input information of the user via the input device.

Specifically, as a signal waveform corresponding to one cycle of the drive signal, there is generated a signal waveform configured including a compressing drive waveform section for operating the piezoelectric element 401 so as to compress the capacity of the fluid chamber 501, and a restoring drive waveform section for operating the piezoelectric element 401 so as to restore the capacity of the fluid chamber 501, which is in the compressed state, to the state prior to the compression.

The signal waveform generation section 30b of the present embodiment is arranged to generate the signal waveform composed of the compressing drive waveform section and the restoring drive waveform section satisfying the following formula 1.

Here, the time length of the compressing signal waveform section is denoted as $T_{red}$, and the time length of the restoring drive waveform section is denoted as $T_{exp}$. Further, average pressure in the fluid chamber 501 in a period of supplying the compressing drive waveform section is denoted as $P_{gen}$, and pressure applied to the entrance channel 503 in the fluid chamber 501 on the pump 20 side in a period of supplying the restoring drive waveform section is denoted as $P_{sup}$.

$$T_{red} \times (P_{gen} - P_{sup}) \leq T_{exp} \times P_{sup} \quad (1)$$

Hereinafter, the formula 1 described above will be explained.

When denoting the cross section of the entrance channel 503 as S, the momentum $M_g$ acting on the entrance channel on the fluid chamber 501 side is expressed as "$M_g = S \times T_{red} \times (P_{gen} - P_{sup})$." On the other hand, the momentum Ms acting on the entrance channel 503 on the pump 20 side is expressed as "$M_s = S \times T_{exp} \times P_{sup}$." Further, in the fluid jet emitting section 2 with the configuration described above, it is known that $P_{sup}$ usually takes a value far smaller than $P_{gen}$ ($P_{gen} \gg P_{sup}$). Therefore, it is also possible to neglect $P_{sup}$ in the formula 1 described above.

Further, in a period (the period of $T_{exp}$) during which the capacity of the fluid chamber 501 is expanding (restoring the original capacity), the average pressure of the fluid chamber 501 becomes 0 atm or nearly 0 atm (hereinafter, this pressure state is referred to as a vacuum state) because the fluid is drawn due to the inertance of the exit channel 511.

In other words, if the momentum $M_s$ provided thereto in the period of $T_{exp}$ is equal to or larger than the momentum $M_g$ provided thereto in the period of $T_{red}$, the fluid can be restored to the original steady state.

Here, the steady state denotes the state in which the fluid flows through the fluid chamber 501 while the supply pressure from the pump 20 and the fluid resistance of the entire channel balance with each other.

Therefore, by supplying the piezoelectric element 401 forming the capacity varying section with the drive signal having a signal waveform, which corresponds to one cycle thereof, and is composed of the compressing drive waveform section with the time length $T_{red}$ and the restoring drive waveform section with the time length $T_{exp}$ satisfying the relationship of formula 1 described above, it is possible to restore the fluid to the original steady state in a period corresponding to one cycle of the drive signal. Thus, it is possible to prevent the compressing drive waveform section in the subsequent cycle from being supplied to the piezoelectric element 401 prior to returning to the steady state, and therefore, the resulting degradation of the fluid jet force can be prevented.

Further, by supplying the drive signal satisfying the formula 1 described above, it is possible to gradually restore (expand) the capacity of the fluid chamber 501 to the original state effectively using the time necessary for restoring the flow rate in the entrance channel 503. Thus, the expansion of the vacuum bubble is prevented, and the gas emission to the vacuum bubble is reduced, and therefore, it is possible to restore the steady state in the condition in which substantially no gas bubble exists in the fluid chamber 501. Thus, it becomes possible to reduce degradation of the fluid jet force caused by degradation of the rigidity of the fluid chamber 501 due to the gas bubbles.

The signal waveform generation section 30b of the present embodiment is further arranged to generate the signal waveform satisfying the formula 1 described above using the waveform information of a plurality of types of sine waves with periods different from each other stored in the data storage section 30c. Here, the waveform information is the data (digital data) obtained by sampling the signal levels (e.g., voltage values) of one cycle of the plurality of types of sine wave signals at time intervals $\Delta t$ (shorter than one cycle).

Specifically, the signal waveform generation section 30b of the present embodiment is arranged to generate the signal waveform by combining the data of a part of each of two sine wave signals with periods different from each other. For example, it generates the signal waveform by splicing the anterior half cycle (T1/2 ($\lambda$1/2)) of one sine wave and the posterior half cycle (T2/2 ($\lambda$2/2)) of the other sine wave with each other.

It should be noted that regarding the waveform information of the sine waves, it is possible to store one or some pieces of basic information, and generate desired waveform information by executing arithmetic processing on the basic information.

The signal waveform generation section 30b of the present embodiment is used, for example, when performing the calibration of the waveform information upon powering on, or in replacing the fluid jet emitting section 2.

Therefore, the signal waveform generation section 30b has a function of determining $T_{red}$ and $T_{exp}$ of the signal waveform corresponding to the jet emission intensity set by the user based on the measurement data from a pressure sensor (not shown) capable of measuring the pressure of the fluid chamber 501, the entrance channel 503, and so on provided to the fluid jet emitting section 2.

Specifically, when generating the signal waveform, the signal waveform generation section 30b first determines $T_{red}$ corresponding to the jet emission intensity set by the user and preliminary $T_{exp}$ based on a data table stored in the data storage section 30c, and then, generates the drive signal waveform based on $T_{red}$ and preliminary $T_{exp}$. Subsequently, the signal waveform generation section 30b drives the pulsation generation section 100 (the piezoelectric element 401) with the drive signal waveform, and measures $P_{gen}$ and $P_{sup}$ at that moment based on the detection data of the pressure sensor. Further, the signal waveform generation section 30b adjusts $T_{exp}$ so that $P_{gen}$ and $P_{sup}$ thus measured satisfy the formula 1 described above. The signal waveform generation section 30b thereafter repeatedly performs generation of the drive signal waveform based on $T_{red}$ thus determined and $T_{exp}$ thus adjusted, driving of the pulsation generation section 100 with the signal waveform thus generated, and adjustment of $T_{exp}$ until $P_{gen}$ and $P_{sup}$ thus measured satisfy the relationship of the formula 1 described above.

Further, the data storage section 30c is configured including a storage medium for storing waveform information described above related to a plurality of types of sine waves with periods and amplitudes different from each other, the data table for determining $T_{red}$ and $T_{exp}$ corresponding to the jet emission intensity thus set, and other data used for processing of respective constituents, and has a function of reading out the data stored in the storage medium in response to a read request from each of the constituents and writing the data in the storage medium in response to a write request from each of the constituents. In other words, in addition to the function as the waveform information storage section, the data storage section 30c also has a function of storing other necessary data.

The drive signal supply section 30d has a function of supplying the drive signal to the piezoelectric element 401 of the capacity varying section forming the pulsation generation section 100 in sync with the sync signal from the sync signal generation section 30e in response to a drive signal supply command from the operation control section 30a.

Specifically, based on waveform designation information included in the supply command, the drive signal supply section 30d reads out the corresponding waveform information (digital waveform data) from the data storage section 30c, executes DA conversion on the waveform information thus read out to generate an analog drive signal, and supplies the piezoelectric element 401 with the drive signal thus generated in sync with the sync signal. It should be noted that the waveform designation information corresponds, for example, to identification information attached to the signal waveform generated in the signal waveform generation section 30b described above.

Further, it is arranged that when a halt command is input from the operation control section 30a in the process of supplying the drive signal, the supply of the drive signal is halted after the entire waveform of one cycle in the midstream of the supply process has been supplied to the piezoelectric element 401.

The sync signal generation section 30e includes an oscillator such as a ceramic oscillator or a crystal oscillator, a counter (or a PLL circuit), and so on, and has a function of generating the sync signal based on a reference clock signal clk, which is a signal output from the oscillator. Further, the sync signal generation section 30e supplies the drive signal supply section 30d with the reference clock signal and the sync signal.

It should be noted that the drive section 30 is provided with a computer system for realizing the functions of the respective constituents described above with software, and for executing the software for controlling the hardware necessary for realizing the functions described above. Although the hardware configuration of the computer system is not shown in the drawings, there is adopted a configuration including a processor, a random access memory (RAM), and a read only memory (ROM), and connecting these elements with various internal and external buses.

Further, a display device such as a CRT or LCD monitor, and an input device such as an operation panel, a mouse, or a keyboard are coupled to the bus via an input/output interface (I/F) such as IEEE1394, USB, or a parallel port.

Further, it is arranged that when powering on, a system program stored in the ROM and so on loads various dedicated computer programs on the RAM, which are previously stored in the ROM, and for realizing the functions of the respective sections, and the processor fully uses various resources along the instructions described in the program loaded on the RAM to perform predetermined controls and arithmetic processing, thereby realizing the functions described above on the software.

Then, with reference to FIG. 6, the flow of the signal waveform generation process in the signal waveform generation section 30b will be explained.

Figure 6:
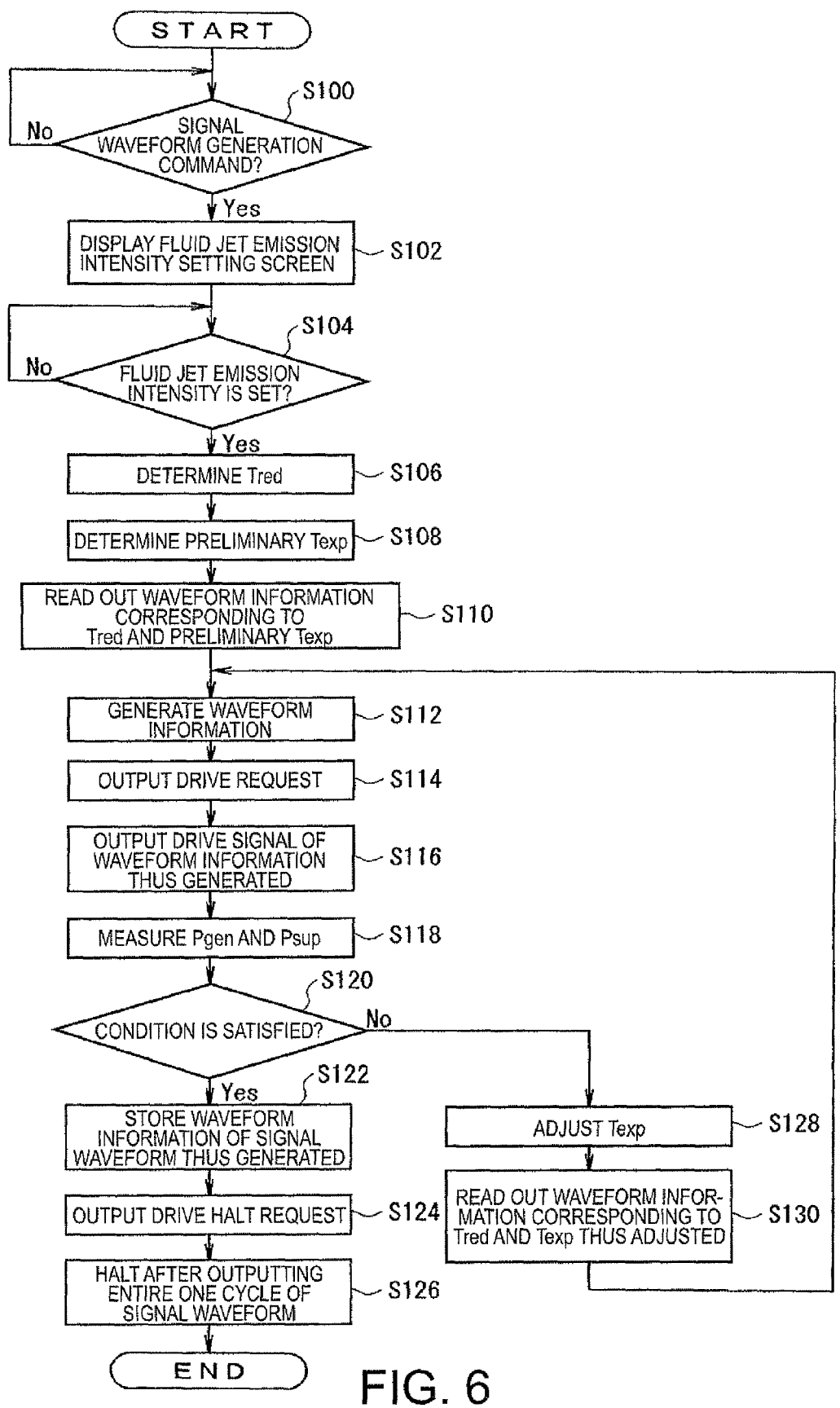
FIG. 6 is a flowchart showing a process of generating a signal waveform in the drive section.

When the processor executes the dedicated program to start the signal generation process, the process first proceeds to the step S100 as shown in FIG. 6.

In the step S100, whether or not a generation command of the signal waveform from the operation control section 30a is input is determined in the signal waveform generation section 30b, and if it is determined that the command is input (Yes), the process proceeds to the step S102, and otherwise (No) the determination process is repeated until the command is input.

In the case of proceeding to the step S102, the signal waveform generation section 30b displays a setting screen for fluid jet emission intensity, and then the process proceeds to the step S104.

In the step S104, whether or not the jet emission intensity is set by the user via the input device is determined in the signal waveform generation section 30b, and if it is determined that the intensity is set (Yes), the process proceeds to the step S106, and otherwise (No) the determination process is repeated until the intensity is set.

In the case of proceeding to the step S106, the signal waveform generation section 30b determines $T_{red}$ corresponding to the jet emission intensity set in the step S104 based on the data table, in which the time length $T_{red}$ of the compressing signal waveform section corresponding to a predetermined jet emission intensity is registered, and which is stored in the data storage section 30c, and then the process proceeds to the step S108.

In the step S108, the signal waveform generation section 30b determines preliminary $T_{exp}$ corresponding to the jet emission intensity set in the step S104 based on the data table, in which the time length $T_{exp}$ of the restoring signal waveform section corresponding to a predetermined type of jet emission intensity is registered, and which is stored in the data storage section 30c, and then the process proceeds to the step S110.

In the step S110, the signal waveform generation section 30b reads out two types of waveform information corresponding respectively to $T_{red}$ determined in the step S105 and $T_{exp}$ preliminarily determined in the step S108 among a plurality of types of sinusoidal waveform information stored in the data storage section 30c, and then the process proceeds to the step S112.

In the step S112, the signal waveform generation section 30b combines the anterior half cycle of one of the signal waveforms generated based on the two types of waveform information read out in the step S110 and the posterior half cycle of the other thereof to generate one cycle of signal waveform, and then the process proceeds to the step S114.

In the step S114, the signal waveform generation section 30b outputs, to the operation control section 30a, a drive request for making the drive signal supply section 30d drive the pulsation generation section 100 with the signal waveform generated in the step S112, and then the process proceeds to the step S116.

In the step S116, the drive signal supply section 30d outputs the drive signal obtained by DA-converting the digital waveform signal (the waveform information) generated in the step S112 into the analog waveform signal to the piezoelectric element 401 of the pulsation generation section 100 in sync with the sync signal from the sync signal generation section 30e in response to the drive command from the operation control section 30a, and then the process proceeds to the step S118.

In the step S118, the signal waveform generation section 30b measures the average pressure $P_{gen}$ in the fluid chamber 501 during the supply period of the compressing drive waveform section and the pressure $P_{sup}$ applied to the entrance channel 503 in the fluid chamber 501 on the pump side during the supply period of the restoring drive waveform section based on the detection data from the pressure sensor provided to the fluid jet emitting section 2 in response to the supply of the drive signal to the piezoelectric element 401 in the step S116, and then the process proceeds to the step S120.

In the step S120, the signal waveform generation section 30b determines whether or not $P_{gen}$ and $P_{sup}$ measured in the step S118, and $T_{red}$ and $T_{exp}$ thus determined satisfy the relationship of the formula 1 described above, and if it is determined that the relationship is satisfied (Yes), the process proceeds to the step S122, and otherwise (No) the process proceeds to the step S128.

In the case of proceeding to the step S122, the signal waveform generation section 30b stores the waveform information of the signal waveform generated in the step S112 in the data storage section 30c in correspondence with the identification information unique to the waveform information, and then the process proceeds to the step S124.

In the step S124, the signal waveform generation section 30b outputs a drive halt request to the operation control section 30a, and then the process proceeds to the step S126.

In the step S126, the drive signal supply section 30d stops the supply of the drive signal after outputting the entire signal waveform corresponding to one cycle, and the series of process is terminated.

On the other hand, in the case in which the condition is not satisfied, and the process proceeds to the step S128 in the step S120, the signal waveform generation section 30b adjusts $T_{exp}$ so as to satisfy the relationship of the formula 1 described above, and then the process proceeds to the step S130.

In the step S130, the signal waveform generation section 30b reads out two types of waveform information corresponding respectively to $T_{red}$ determined in the step S106 and $T_{exp}$ adjusted in the step S122 among a plurality of types of sinusoidal waveform information stored in the data storage section 30c, and then the process proceeds to the step S112.

It should be noted that it is also possible to set the fluid jet emission intensity in the steps S102 and S104 by designating the range corresponding to the performance of the fluid jet emitting section 2. On this occasion, it should be arranged that the process of the steps S106 through S124 is repeated for every jet emission intensity in the range thus set.

Then, with reference to FIG. 7, the flow of the drive signal supply process in the drive signal supply section 30d will be explained.

Figure 7:
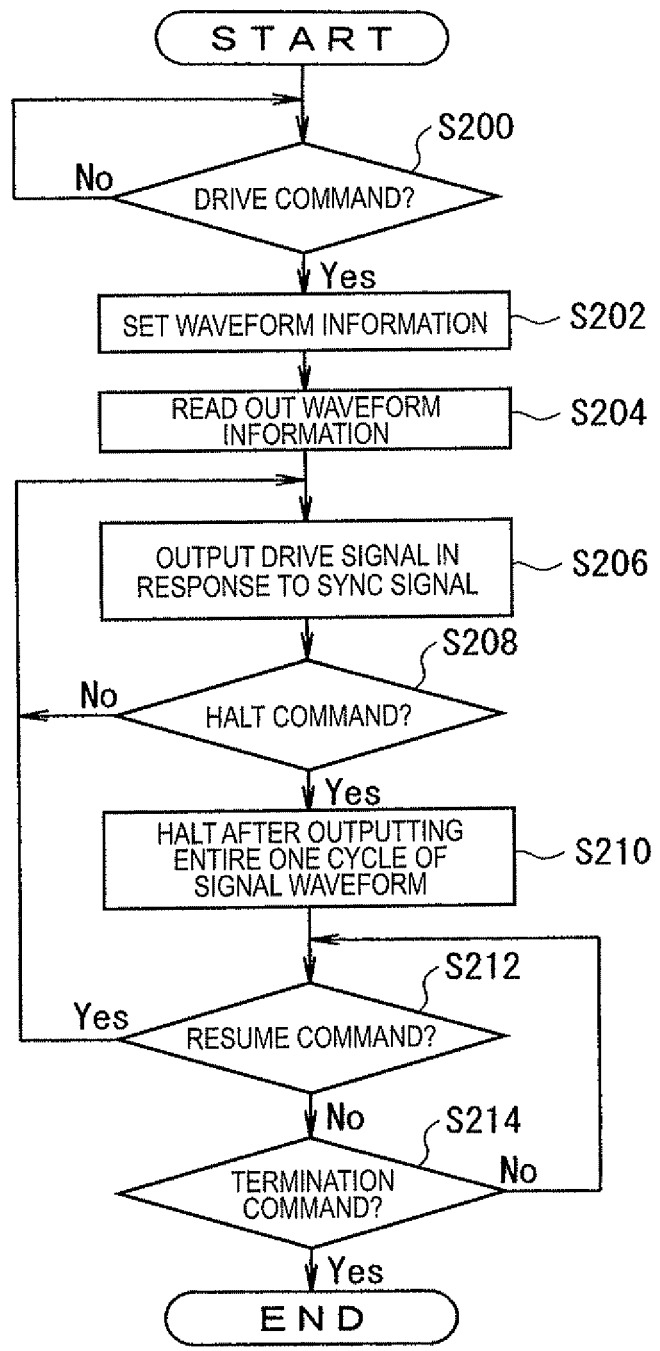
FIG. 7 is a flowchart showing a process of supplying the pulsation generation section with a drive signal in the drive section.

When the processor executes the dedicated program to start the drive signal supply process, the process first proceeds to the step S200 as shown in FIG. 7.

In the step S200, the drive signal supply section 30d determines whether or not a drive command from the operation control section 30a is input, and if it is determined that the command is input (Yes), the process proceeds to the step S202, and otherwise (No) the process proceeds to the step S200.

In the case of proceeding to the step S202, the drive signal supply section 30d sets the waveform information of the waveform type used for driving the fluid jet emitting section 2 based on the identification information of the designated waveform included in the drive command, and then the process proceeds to the step S204.

In the step S204, the drive signal supply section 30d reads out the waveform information of the waveform type, which is set in the step S202, from the data storage section 30c, and then the process proceeds to the step S206.

In the step S206, the drive signal supply section 30d outputs the drive signal obtained by DA-converting the digital waveform signal thus read out into the analog waveform signal to the piezoelectric element 401 of the pulsation generation section 100 in sync with the sync signal from the sync signal generation section 30e, and then the process proceeds to the step S208.

In the step S208, the drive signal supply section 30d determines whether or not a halt command is input from the operation control section 30a, and if it is determined that the command is input (Yes), the process proceeds to the step S210, and otherwise (No) the output process of the drive signal in the step S206 is continued.

In the case of proceeding to the step S210, the drive signal supply section 30d stops the supply of the drive signal after outputting the entire signal waveform corresponding to one cycle, and then the process proceeds to the step S212.

In the step S212, the drive signal supply section 30d determines whether or not a resume command is input from the operation control section 30a, and if it is determined that the command is input (Yes), the process proceeds to the step S206 to resume the output process of the drive signal, and otherwise (No) the process proceeds to the step S214.

In the case of proceeding to the step S214, whether or not a termination command is input from the operation control section 30a is determined, and if it is determined that the command is input (Yes), the drive signal supply process is terminated, and otherwise (No) the process proceeds to the step S212.

Then, with reference to FIG. 8, a specific operation of the fluid jet device 1 of the present embodiment will be explained.

Figure 8:
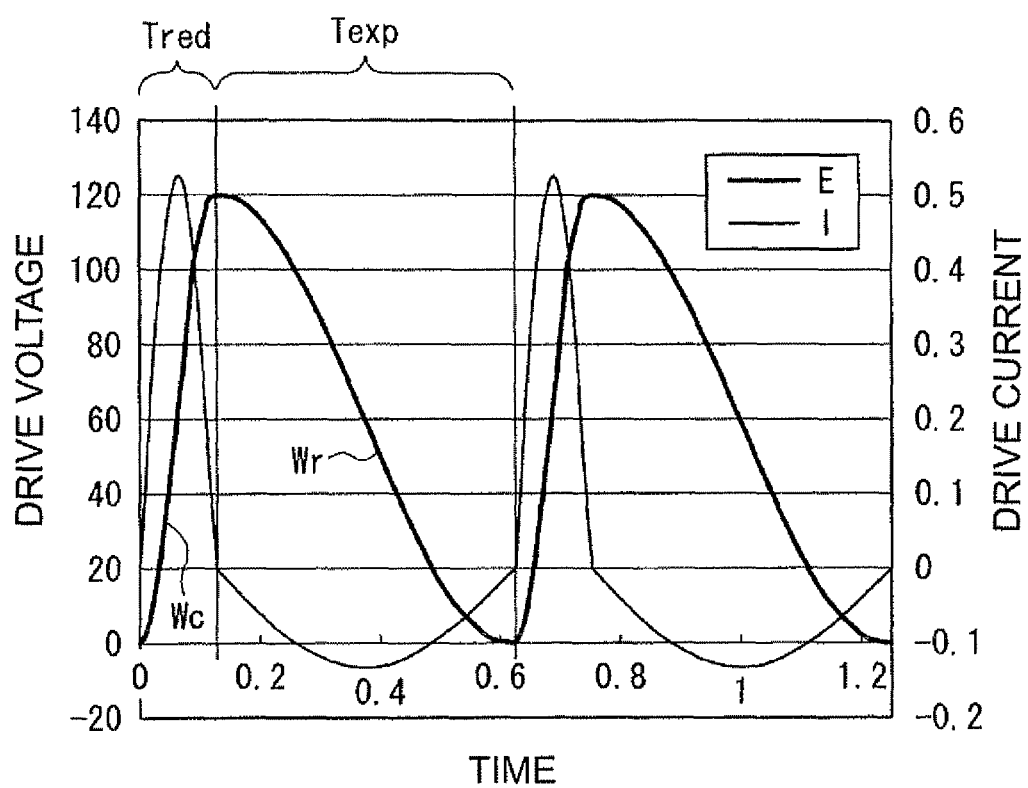
FIG. 8 is a diagram showing an example of the signal waveform generated by combining two types of sine waves.

Here, FIG. 8 is a diagram showing an example of the signal waveform generated by combining two types of sine waves.

Firstly, a specific operation of the signal waveform generation process will be explained.

When a calibration instruction of the signal waveform from the user is input to the drive section 30 via the input device, the operation control section 30a outputs the generation command of the signal waveform to the signal waveform generation section 30b.

Meanwhile, when receiving the generation command of the signal waveform, the signal waveform generation section 30b proceeds to the setting process of the fluid jet emission intensity (the branch of "Yes" in the step S100).

The signal waveform generation section 30b first displays (step S102) the setting screen of the fluid jet emission intensity desired by the user on the display section not shown, thereby prompting the user to set the jet emission intensity.

When the jet emission intensity is set (the branch of "Yes" in the step S104) in accordance with the input information of the user via the input device, the signal waveform generation section 30b determines (step S106) $T_{red}$ (corresponding to the nearest value to the jet emission intensity thus set) corresponding to the jet emission intensity thus set, based on the data table, which is stored in the data storage section 30c, and for determining $T_{red}$.

Subsequently, the signal waveform generation section 30b determines (step S108) preliminary $T_{exp}$ (corresponding to the nearest value to the jet emission intensity thus set) corresponding to the jet emission intensity thus set based on the data table, which is stored in the data storage section 30c, and for preliminarily determining $T_{exp}$.

When $T_{red}$ and preliminary $T_{exp}$ are determined, the signal waveform generation section 30b then reads out the waveform information of the anterior half cycle of the sine wave sin 1 with a period nearest to the double (e.g., 0.2 [ms]) of $T_{red}$ thus determined and the waveform information of the posterior half cycle of the sine wave sin 2 with a period nearest to the double of preliminary $T_{exp}$ thus determined from the data storage section 30c (step S110).

Then, the signal waveform generation section 30b combines the two types of waveform information thus read out, thereby generating the waveform information of the signal waveform with the compressing drive waveform section having the time length of $T_{red}$ determined as described above, and the restoring drive waveform section having the time length of $T_{exp}$ preliminarily determined as described above (step S112).

When the signal waveform is generated, the signal waveform generation section 30b outputs, to the operation control section 30a, the drive request for making the drive signal supply section 30d drive the piezoelectric element 401 of the pulsation generation section 100 with the signal waveform thus generated (step S114).

Thus, the operation control section 30a outputs, to the drive signal supply section 30d, the drive signal supply command for supplying the drive signal of the signal waveform thus generated to the piezoelectric element 401.

Meanwhile, when receiving the drive signal supply command of the signal waveform thus generated as described above from the operation control section 30a, the drive signal supply section 30d executes the DA conversion on the waveform information included in the drive signal supply command in sync with the sync signal from the sync signal generation section 30e, and then outputs the analog signal obtained by executing the DA conversion to the piezoelectric element 401 of the pulsation generation section 100 as the drive signal (step S116).

When supply of the drive signal to the piezoelectric element 401 is started, the signal waveform generation section 30b measures the average pressure $P_{gen}$ in the fluid chamber 501 and the pressure $P_{sup}$ applied to the entrance channel 503 in the fluid chamber 501 on the pump 20 side, based on the detection data from the pressure sensor provided to the fluid jet emitting section 2 (step S118).

Then, the signal waveform generation section 30b determines whether or not $P_{gen}$ and $P_{sup}$ thus measured satisfy the relationship of the formula 1 described above (step S120).

For example, it is assumed that $P_{gen}$=12 atm (1.2 MPa) and $P_{sup}$=2 atm (0.2 MPa) are obtained based on the detection data of the pressure sensor.

On this occasion, according to the formula 1 described above, "0.1×(12−2)≦$T_{exp}$×2," namely "0.5≦$T_{exp}$" is obtained. Therefore, if $T_{exp}$ is no larger than 0.5 [ms], it is determined that the relationship of the formula 1 described above is not satisfied (the branch of "No" in the step S120).

For example, if present $T_{exp}$ is 0.4 [ms], it is determined that the relationship of the formula 1 described above is not satisfied, and an adjustment such as adding 0.1 [ms] to present $T_{exp}$ (0.4 [ms]) is executed (step S128). Further, the signal waveform generation section 30b reads out the waveform information corresponding to $T_{red}$ thus determined and $T_{exp}$ thus adjusted as described above from the data storage section 30c (step S130), and then the waveform information with adjusted $T_{exp}$ is generated based on the waveform information described above (step S112).

Specifically, as illustrated by a heavy line in FIG. 8, there is generated a combined waveform obtained by connecting the maximum value of the anterior half cycle ($\lambda/2$) of the sine wave sin 1 forming the compressing drive waveform section Wc in one cycle of the signal waveform, and the maximum value of the posterior half cycle ($\lambda/2$) of the sine wave sin 2 forming the restoring drive waveform section Wr therein.

The signal waveform generation section 30b outputs a drive request to the operation control section 30a so as to drive the piezoelectric element 401 with the signal waveform of the waveform information thus generated (step S114). Thus, the piezoelectric element 401 is driven with the signal waveform thus adjusted (step S116), and $P_{gen}$ and $P_{sup}$ are measured again based on the detection data of the pressure sensor (step S118).

Then, if $P_{gen}$=12 atm (1.2 MPa) and $P_{exp}$=2 atm (0.2 MPa) are obtained, since $T_{red}$ has been set to be 0.1 [ms] and $T_{exp}$ has been set to be 0.5 [ms] in this case, it is determined that the relationship of the formula 1 described above is satisfied (the branch of "Yes" in the step S120).

When it is determined that $T_{red}$ and $T_{exp}$ satisfy the relationship of the formula 1 described above, the signal waveform generation section 30b stores the waveform information of one cycle of the signal waveform corresponding to these $T_{red}$ and $T_{exp}$ into the data storage section 30c in correspondence with the identification information (step S122).

It should be noted that on this occasion, it is also possible to determine $T_{exp}$ to be a value equal to or larger than 0.5 [ms] with respect to $T_{red}$ of 0.1 [ms].

Further, the waveform information is not limited to be of one cycle, but it is also possible to arrange that a plurality of cycles of waveform information is stored. In this case, in the waveforms each corresponding to one cycle and adjacent to each other, the lowest value of the compressing drive waveform section of one of the waveforms and the lowest value of the restoring drive waveform section of the other of the waveforms are connected to each other.

When the waveform information satisfying the relationship of the formula 1 is stored, the signal waveform generation section 30b outputs, to the operation control section 30a, the drive halt request for stopping the piezoelectric element 401 in operation (step S124).

Thus, the operation control section 30a outputs, to the drive signal supply section 30d, a drive signal supply halt command for stopping the supply of the drive signal to the piezoelectric element 401.

Meanwhile, when receiving the drive signal supply halt command from the operation control section 30a, the drive signal supply section 30d stops supplying the drive signal after outputting one whole cycle of the signal waveform.

Then, a specific operation of the drive signal supply process will be explained.

When the user holds down a drive switch (not shown), and the drive signal supply instruction is input to the drive section 30, the operation control section 30a outputs the drive signal supply command to the drive signal supply section 30d.

Meanwhile, when receiving the drive signal supply command, the drive signal supply section 30d proceeds to the waveform information setting process (the branch of "Yes" in the step S200).

Since the drive signal supply command includes designated waveform information including the identification information of the waveform information used as the drive signal, the drive signal supply section 30d sets the waveform information with the identification information corresponding to the designated waveform information as the waveform information used for driving (step S202). Here, it is assumed that the waveform information of the signal waveform illustrated by the heavy line shown in FIG. 8 and generated as described above is set.

When the waveform information used as the drive signal is set, the drive signal supply section 30d subsequently reads the waveform information corresponding to the waveform information thus set out from the data storage section 30c on a working memory such as the RAM (step S204). Subsequently, the drive signal supply section 30d executes the DA conversion on the waveform information thus read out on the working memory in sync with the sync signal from the sync signal generation section 30e, and outputs the analog signal, which is thus converted in the DA conversion, to the piezoelectric element 401 of the pulsation generation section 100 as the drive signal (step S206).

Before the drive signal is supplied, the pump 20 always supplies the entrance channel 503 with the fluid at constant fluid pressure. As a result, when the piezoelectric element 401 does not operate, the fluid flows into the fluid chamber 501 due to the difference between the ejection force of the pump 20 and the fluid resistance value of the entire channel on the entrance channel side.

Here, if the drive signal is input to the piezoelectric element 401 and the piezoelectric element 401 rapidly expands in the period of $T_{red}$ (0.1 [ms]), the pressure inside the fluid channel 501 rises rapidly up to several tens of atm, providing the inertances L1, L2 on the entrance channel side and the exit channel side have sufficiently large values.

Since the pressure is far stronger than the pressure applied by the pump 20 to the entrance channel 503, the inflow of the fluid from the entrance channel side into the fluid chamber 501 is reduced by the pressure, and the outflow thereof from the exit channel 511 is increased.

However, since the inertance L1 of the entrance channel 503 is larger than the inertance L2 of the exit channel 511, and therefore, the increased amount of the fluid ejected from the exit channel is larger than the decreased amount of the amount of flow of the fluid inflowing in the fluid chamber 501 from the entrance channel 503, pulsed fluid ejection, namely a pulsation flow occurs in the connection channel 201. The pressure pulsation in the ejection operation propagates in the connection channel tube 200, and thus the fluid jet is emitted from the fluid jet opening section 212 of the nozzle 211 at the tip of the connection channel tube 200.

Here, since the diameter of the fluid jet opening section 212 of the nozzle 211 is smaller than the diameter of the exit channel 511, the fluid jet is emitted as a further high-pressure, high-speed, and pulsed droplet.

Meanwhile, inside the fluid chamber 501, there is provided a vacuum state immediately after the rise in pressure due to the interaction between decrease in the amount of the fluid inflowing from the entrance channel 503 and increase in the amount of the fluid outflowing from the exit channel 511.

On the other hand, after the rise in pressure, in the period of $T_{exp}$ (0.5 [ms]), the piezoelectric element 401 in the expanded state slowly shrinks taking time five times as long as the time $T_{red}$ (0.1 [ms]) in the expanding process. Thus, since the expansion of the vacuum bubbles is prevented, the flow of the fluid restores the steady state prior to the supply of the drive signal while preventing generation of gases inside the fluid chamber 501.

It should be noted that due to the fact that the fluid chamber 501 has a shape like a solid of revolution and is provided with the entrance channel 503 and the fact that the exit channel 511 is opened in the vicinity of the rotational axis of the shape like a solid of revolution, the swirling flow occurs in the fluid chamber 501, and the bubbles (the vacuum bubbles and the gas bubbles) included in the fluid are immediately discharged from the exit channel 511 to the outside.

Therefore, by continuously supplying the piezoelectric element 401 with the drive signal having the signal waveform illustrated by the heavy line shown in FIG. 8, it is possible to continuously emit jet of the pulsation flow from the nozzle 211 in the state of maintaining strong jet force.

Further, as illustrated by the waveform of a thin line shown in FIG. 8, the level of the drive current in the period of $T_{exp}$ can be suppressed to a lower level compared to the level of the drive current in the period of $T_{red}$. Therefore, in the case in which a bridge circuit or the like is used as the drive circuit for driving the piezoelectric element 401, since a rated value of the maximum peak current of a current emitting transistor (e.g., the transistor on the low side) among the transistors used in the circuit can be suppressed to a lower level, the cost for the transistor can be reduced.

Further, since it is arranged that the signal waveform of one cycle of drive signal is generated as a combination of sine waves as illustrated by the waveform of the heavy line shown in FIG. 8, it is possible to smoothly couple signal waveforms with periods different from each other, and to reduce the stress to the mechanism of the fluid jet emitting section 2.

Further, since the signal waveform generation section 30b is capable of generating the waveform information of the appropriate signal waveform in accordance with the values of $P_{gen}$ and $P_{sup}$ of the fluid jet emitting section 2, it is possible to easily perform replacement with a fluid jet emitting section with different $P_{gen}$ and $P_{sup}$.

Second Embodiment

Figure 9A:
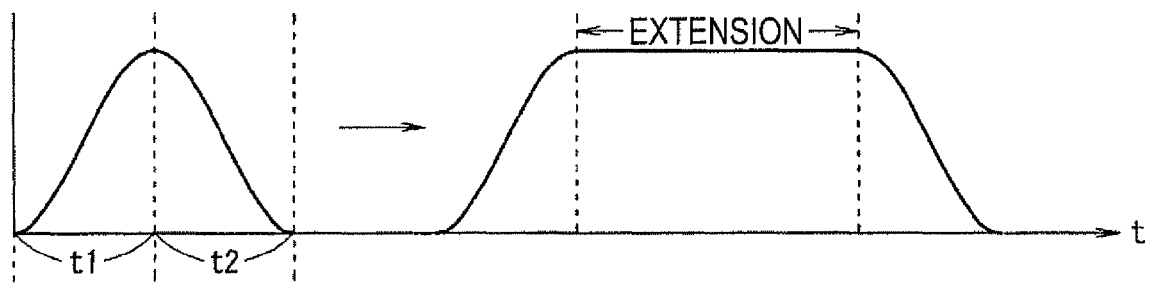
FIG. 9A is a diagram showing an example of a method of expanding a waveform.
Figure 9B:
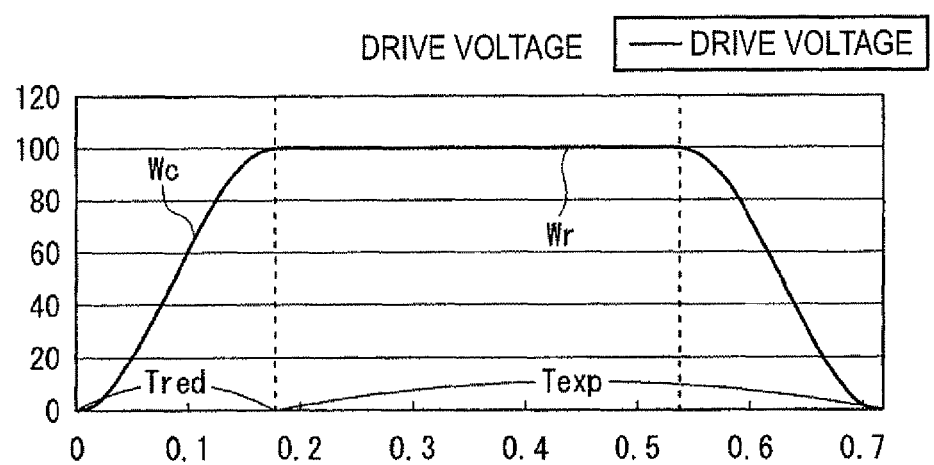
FIG. 9B is a diagram showing an example of a signal waveform of a drive signal according to a second embodiment.

Hereinafter, a second embodiment of the invention will be explained with reference to the accompanying drawings. FIGS. 9A and 9B are diagrams showing a fluid jet device, a drive device of the fluid jet device, a surgical instrument, and a method of driving the fluid jet device according to the second embodiment of the invention.

In comparison with the first embodiment described above, the present embodiment is different therefrom in a part of the method of forming the signal waveform satisfying the relationship of the formula 1 in the signal waveform generation section 30b of the drive section 30. Therefore, since the other part of the configuration is substantially the same as in the drive section 30 of the first embodiment described above, hereinafter the different part will be explained in detail, and the explanations of the duplicated part will be omitted if appropriate.

The signal waveform generation section 30b of the present embodiment is arranged to generate the signal waveform having a waveform section disposed between the compressing drive waveform section and the restoring drive waveform section by expanding a part of the restoring drive waveform section, the waveform section having an output level for driving the piezoelectric element 401 so as to keep (stop the capacity variation) the capacity of the fluid chamber 501 after the fluid chamber 501 is compressed.

Here, FIG. 9A is a diagram showing an example of a method of expanding the waveform, and FIG. 93 is a diagram showing an example of a signal waveform of a drive signal according to the present embodiment.

Specifically, the signal waveform generation section 30b generates the signal waveform of the waveform shape as shown in FIG. 9B having the anterior half cycle t1 of the sine wave signal shown in FIG. 9A as the compressing drive waveform section with the time length $T_{red}$ (t1=$T_{red}$) satisfying the relationship of the formula 1 described above, a waveform section including an extension section obtained by extending the period with the maximum value in the posterior half cycle t2 (t1=t2) of the same sine wave signal so as to be the period of $T_{exp}$ satisfying the relationship of the formula 1 described above as the restoring drive waveform section.

In other words, since the expansion of the vacuum bubble becomes apt to occur by the rapid expansion of the capacity of the fluid chamber 501 due to a rapid shrinkage operation subsequent to the expansion operation (capacity compression operation) of the piezoelectric element 401, by keeping the expanded state of the piezoelectric element after the capacity compression operation, it is possible to prevent the expansion of the vacuum bubbles and generation of the gas bubbles. Further, since it leads to waiting for the vacuum bubbles to disappear in the compressed state, it is possible to make the vacuum bubbles disappear in a shorter period of time than in the first embodiment described above, and therefore, it is possible to restore the steady state in a shorter period of time than in the first embodiment described above.

The flow of the signal waveform generation process of the present embodiment will hereinafter be explained.

The signal waveform generation process of the present embodiment is different from that of the first embodiment described above only in the process content of the steps S110, S112, and S130 in the flowchart shown in FIG. 6, and the same in the process of the other steps.

Hereinafter, the process of the steps S110 and S112 of the present embodiment will be explained.

In the step S110, the signal waveform generation section 30b reads out the waveform information corresponding to $T_{red}$ determined in the step S106 among a plurality of types of sinusoidal waveform information stored in the data storage section 30c, and then the process proceeds to the step S112.

In the step S112, the signal waveform generation section 30b generates the signal waveform obtained by extending the posterior half cycle of the waveform information read out in the step S110 based on $T_{exp}$ thus preliminarily determined in the step S108, and the process proceeds to the step S114.

It should be noted that in the step S130 the signal waveform obtained by extending the posterior half cycle of the waveform information corresponding to $T_{red}$ based on $T_{exp}$ thus adjusted.

Here, if the waveform information corresponding to $T_{red}$ does not exist, the nearest one is read out, and then corrected for use therein.

Then, with reference to FIGS. 9A and 9B, a specific operation of the fluid jet device 1 of the present embodiment will be explained.

Firstly, a specific operation of the signal waveform generation process will be explained.

Since the determination process of $T_{red}$ and the preliminary determination process of $T_{exp}$ are the same as in the first embodiment described above, the process subsequent to the determination will be explained.

When $T_{red}$ and preliminary $T_{exp}$ are determined, the signal waveform generation section 30b then reads out the waveform information of the anterior half cycle of the sine wave sin1 having one cycle the nearest to the double (e.g., 0.2 [ms]) of $T_{red}$ thus determined from the data storage section 30c (step S110).

Subsequently, the signal waveform generation section 30b generates the waveform information of the signal waveform obtained by extending the period with the maximum value in the posterior half cycle in the waveform information thus read out so that the posterior half cycle becomes to have a period equal to or longer than at least $T_{exp}$ thus preliminarily determined (step S112).

Since the subsequent process (steps S114 through S120, and S128) is substantially the same as in the first embodiment, the process after adjusting $T_{exp}$ in the step S128 will be explained.

After adjusting $T_{exp}$, the signal waveform generation section 30b reads out the waveform information of a trapezoidal wave corresponding to the cycle double of $T_{red}$ thus determined as described above from the data storage section 30c (step S130), and corrects the waveform information thus read out so that the time length between nodal points C and E of the waveform information becomes $T_{exp}$ thus adjusted, thereby generating the waveform information after $T_{exp}$ is adjusted (step S112).

Then, the signal waveform generation section 30b outputs the drive request (step S114) to make the drive signal supply section 30d drive the piezoelectric element 401 with the signal waveform of the waveform information thus generated (step S116).

When the drive signal is supplied to the piezoelectric element 401, the signal waveform generation section 30b measures $P_{gen}$ and $P_{sup}$ (step S118), and determines whether or not the measurement results, $T_{red}$, and $T_{exp}$ thus adjusted satisfy the relationship of the formula 1 described above (step S120).

In the determination, if the waveform information with $T_{exp}$ adjusted satisfies the relationship of the formula 1 described above (the branch of "Yes" in the step S120), the signal waveform generation section 30b stores the waveform information into the data storage section 30c in correspondence with the identification number (step S122). The subsequent process of the steps S124 and S126 is substantially the same as in the first embodiment, and therefore the explanations therefor will be omitted.

When $T_{exp}$ is adjusted so as to satisfy the relationship of the formula 1 described above, the signal waveform generation section 30b reads out the waveform information corresponding to $T_{red}$ thus determined as described above from the data storage section 30c (step S130), and extends the posterior half cycle of the waveform information, thus read out, based on $T_{exp}$ thus adjusted, thereby generating the waveform information with $T_{exp}$ adjusted (step S112).

Specifically, as shown in FIG. 9B, the signal waveform generation section 30b generates the signal waveform with the waveform shape in which the period with the maximum value of the restoring drive waveform section continues for about 0.4 [ms].

The waveform information of the signal waveform corresponding to one cycle thus generated is stored in the data storage section 30c in correspondence with the identification number (step S122). It should be noted that the waveform information is not limited to be of one cycle, but it is also possible to arrange that a plurality of cycles of waveform information is stored. In this case, in the waveforms each corresponding to one cycle and adjacent to each other, the lowest value of the compressing drive waveform section of one of the waveforms and the lowest value of the restoring drive waveform section of the other of the waveforms are connected to each other.

The operation of the drive signal supply process is substantially the same as in the first embodiment described above, and therefore the explanations therefor will be omitted.

As described above, by supplying the drive signal with the signal waveform shown in FIG. 9B thus generated as described above to the piezoelectric element 401 of the pulsation generation section 100 to keep the expanded state of the piezoelectric element after rapidly expanding the piezoelectric element to compress the capacity of the fluid chamber 501 in the period of the compressing drive waveform section for 0.1 [ms], it is possible to prevent the expansion of the vacuum bubbles, and consequently generation of the gas bubbles.

Third Embodiment

Hereinafter, a third embodiment of the invention will be explained with reference to the accompanying drawings. FIGS. 10 through 14 are diagrams showing a fluid jet device, a drive device of the fluid jet device, a surgical instrument, and a method of driving the fluid jet device according to the third embodiment of the invention.

In comparison with the first and second embodiments, the present embodiment is different therefrom in the content of the waveform information stored in the data storage section 30c of the drive section 30, a part of the method of generating the signal waveform satisfying the relationship of the formula 1 described above in the signal waveform generation section 30b of the drive section 30, and the method of supplying the drive signal in the drive signal supply section 30d of the drive section 30. Therefore, since the other part of the configuration is substantially the same as in the drive section 30 of the first and second embodiments described above, hereinafter the different part will be explained in detail, and the explanations of the duplicated part will be omitted if appropriate.

The signal waveform generation section 30b of the present embodiment has a function of generating a signal waveform to be a trapezoidal wave with a shape suitable for determining $T_{red}$ and $T_{exp}$ satisfying the relationship of the formula 1 described above using the waveform information of the trapezoidal wave, a data table, and measurement data stored in the data storage section 30c based on the jet emission intensity of the fluid jet emitting section 2, which is set based on the input information of the user via the input device, and driving the pulsation generation section 100.

Specifically, similarly to the case of the first embodiment, the signal waveform generation section 30b generates the signal waveform of the trapezoidal wave having the compressing drive waveform section of the time length $T_{red}$ and the restoring drive waveform section of the time length $T_{exp}$ satisfying the relationship of the formula 1 described above. Then, the signal waveform generation section 30b stores the nodal information of the trapezoidal wave thus generated into the data storage section 30c as the waveform information.

The data storage section 30c of the present embodiment is configured including a storage medium for storing the nodal information (time, voltage levels) of one cycle of a plurality of types of trapezoidal waves with periods and amplitudes different from each other as the waveform information, and in addition, other data used for processing of respective constituents, and has a function of reading out the data stored in the storage medium in response to a read request from each of the constituents and writing the data in the storage medium in response to a write request from each of the constituents.

Then, with reference to FIG. 10, a detailed configuration of the drive signal supply section 30d of the present embodiment will be explained.

Figure 10:
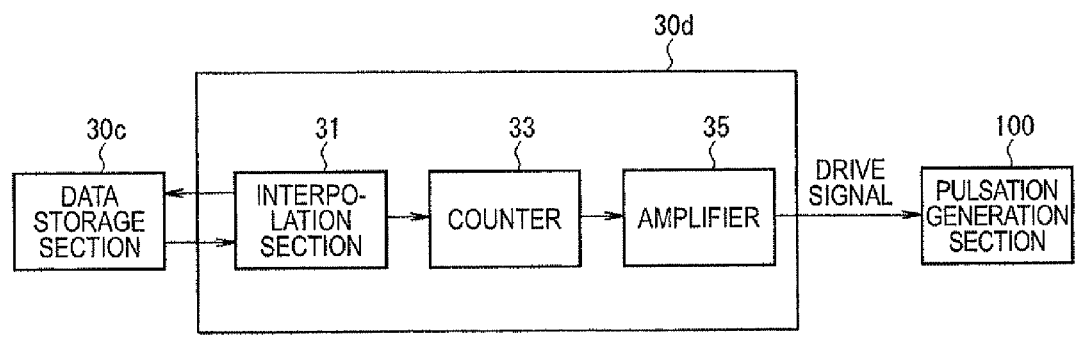
FIG. 10 is a block diagram showing a detailed configuration of a drive signal supply section according to a third embodiment.

Here, FIG. 10 is a block diagram showing the detailed configuration of the drive signal supply section 30d according to the present embodiment.

As shown in FIG. 10, the drive signal supply section 30d of the present embodiment has a configuration including an interpolation section 31, a counter 33, and an amplifier 35.

The interpolation section 31 has a function of reading out the nodal information of the trapezoidal wave used as the drive signal from the data storage section 30c in response to the drive signal supply command from the operation control section 30a, and then setting an operating condition of the counter 33 for supplying the pulsation generation section 100 with the drive signal based on the nodal information.

Figure 11:
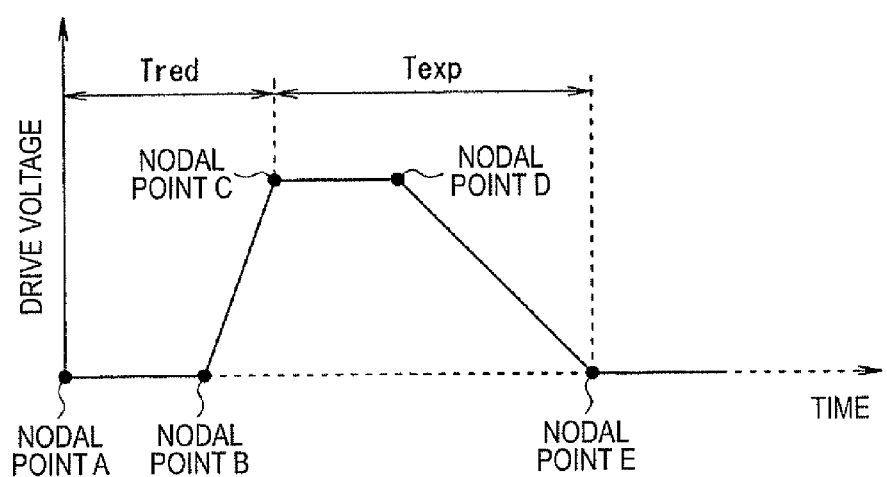
FIG. 11 is a diagram showing an example of a trapezoidal wave forming the drive signal.

Here, FIG. 11 is a diagram showing an example of the trapezoidal wave forming the drive signal.

The data storage section 30c stores the voltage information and the time information of each of the nodal points A through E of the trapezoidal wave shown in FIG. 11 as the waveform information. The waveform information of the nodal points A through C forms the compressing drive waveform section, and the waveform information of the nodal points C through E forms the restoring drive waveform section. Further, in the case in which the time information is the information of the absolute time, $T_{red}$ is defined as the time period corresponding to the difference obtained by subtracting the absolute time of the nodal point A from the absolute time of the nodal point C, and $T_{exp}$ is defined as the time period corresponding to the difference obtained by subtracting the absolute time of the nodal point C from the absolute time of the nodal point E.

Further, the operating condition of the counter corresponds to a condition for interpolating the waveform data between the nodal points adjacent to each other with the resolution of the clock signal clk using the waveform information of each of the nodal points, and then performing the DA conversion from the information of each of the nodal points of the trapezoidal wave into the signal information of the continuous analog trapezoidal wave. Therefore, as the operating condition of the counter, an initial value of counting, the number of times (the time direction) of increase and decrease of counting, an amount (the voltage direction) of increase and decrease of counting, and so on are set.

The counter 33 has a function of performing counting operation of the clock signal clk from the sync signal generation section 30e based on the operating condition set by the interpolation section 31, and then outputting the signal of the count value corresponding to the operating condition to the amplifier 35.

The amplifier 35 has a function of amplifying the signal input from the counter 33 to be in a level appropriate for driving the piezoelectric element 401, and then outputting it to the piezoelectric element 401 of the pulsation generation section 100.

Then, with reference to FIG. 12, the flow of the drive signal supply process in the drive signal supply section 30d of the present embodiment will be explained.

Figure 12:
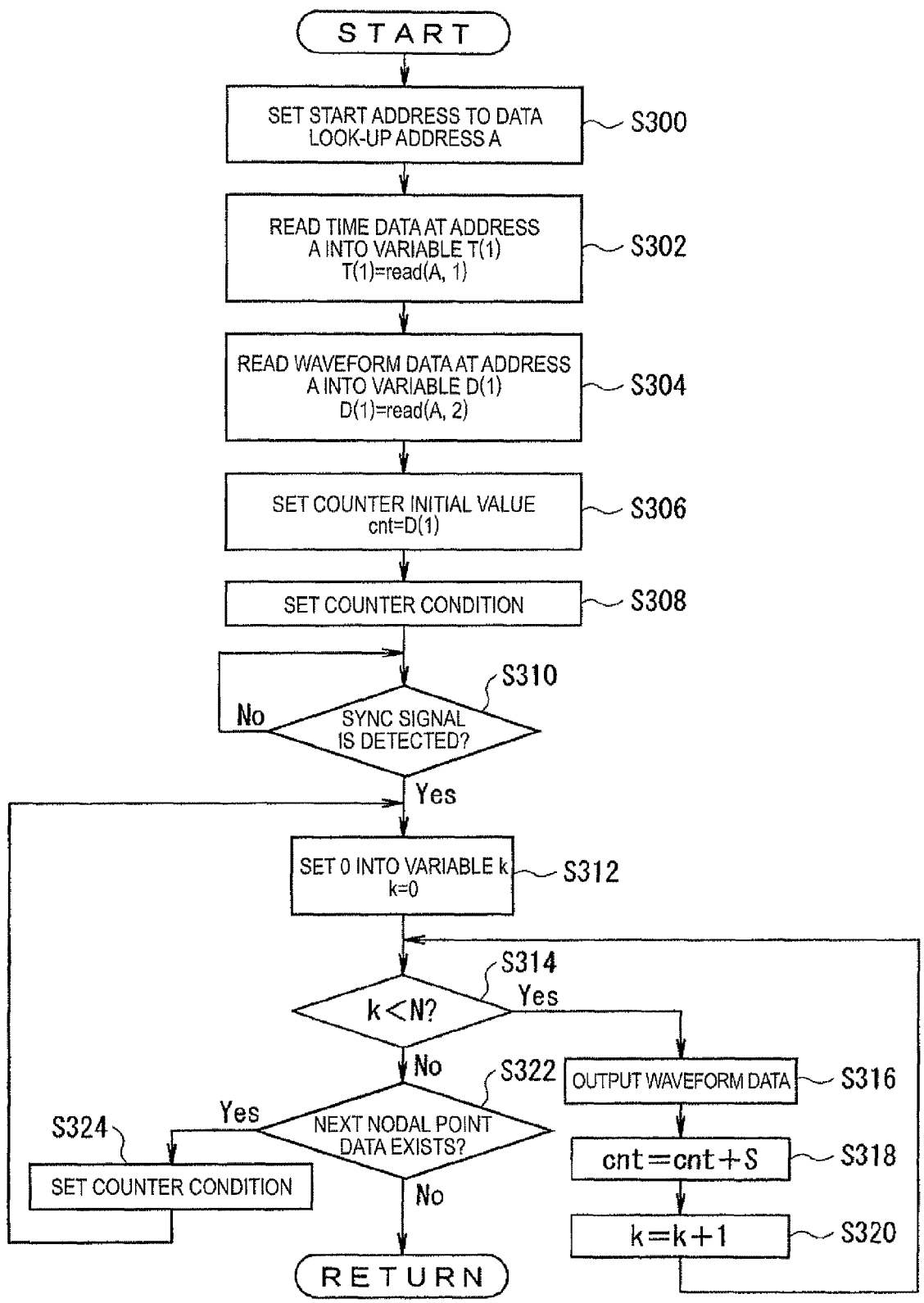
FIG. 12 is a flowchart showing a process of outputting the drive signal in a drive signal supply process of the third embodiment.

Here, FIG. 12 is a flowchart showing a process (corresponding to the steps S204 and S206 of the first embodiment described above) of outputting the drive signal in the drive signal supply process of the present embodiment.

When the drive signal output process is started, as shown in FIG. 12, the process firstly proceeds to the step S300.

In the step S300, the interpolation section 31 sets a start address of the waveform information, which is set as the drive signal, in a data look-up address A, and then the process proceeds to the step S302.

In the step S302, the interpolation section 31 reads the time data "read (A, 1)" at the address A into a variable T(1), and then the process proceeds to the step S304.

Thus, "T(1)=read (A, 1)" is obtained.

In the step S304, the interpolation section 31 reads the waveform data "read (A, 2)" at the address A into a variable D(1), and then the process proceeds to the step S306.

Thus, "D(1)=read (A, 2)" is obtained.

In the step S306, the interpolation section 31 sets the value of D(1), which is read in the step S304, in a variable cnt as the initial value of the counter, and then the process proceeds to the step S308.

Thus, "cnt=D(1)=read (A, 2)" is obtained.

In the step S308, the interpolation section 31 executes a counter condition setting process described later to set the counter condition, and then the process proceeds to the step S310.

In the step S310, the interpolation section 31 determines whether or not the sync signal is detected, and if it is determined that the sync signal is detected (Yes), the process proceeds to the step S312, and otherwise (No) the determination process is repeated until the sync signal is detected.

If the process proceeds to the step S312, the interpolation section 31 sets "0" in a variable k, and then the process proceeds to the step S314. Here, the variable k is a variable for counting the number of times of the counting by the counter.

In the step S314, the counter 33 determines whether or not the value of the variable k is smaller than the value of a variable N, and if it is determined that it is smaller (Yes), the process proceeds to the step S316, and otherwise (No) the process proceeds to the step S322. Here, the variable N is a variable in which the number of times of the counting in the time axis necessary for moving from a certain nodal point to the next nodal point is set, and is set in the counter condition setting process described later.

If the process proceeds to the step S316, the counter 33 outputs the signal waveform to the amplifier 35, and then the process proceeds to the step S318.

In the step S318, the interpolation section 31 adds the value of a variable S to the present value of the variable cnt, and then the process proceeds to the step S320. Here, the variable S is a variable in which the amount of increase and decrease of the counting in the voltage axis in each counting operation in a period from a certain nodal point to the next nodal point is set, and is set in the counter condition setting process described later. If the value of the variable S is a positive number, the counter 33 counts up the value of the variable S, and if the value of the variable S is a negative number, the counter 33 counts down the absolute value of the variable S.

In the step S320, the interpolation section 31 adds 1 to the present value of the variable k, and then the process proceeds to the step S314.

On the other hand, if the value of the variable k exceeds the value of the variable N in the step S314, and the process proceeds to the step S322, the interpolation section 31 determines whether or not the next nodal point data exists, and if it is determined that it exists (Yes), the process proceeds to the step S324, and otherwise (No) the series of process is terminated, and the process returns to the original process.

If the process proceeds to the step S324, the interpolation section 31 executes the counter condition setting process to set the counter condition, and then the process proceeds to the step S312.

Then, with reference to FIG. 13, the flow of the counter condition setting process in the steps S308, S324 will be explained.

Figures 13, 14:
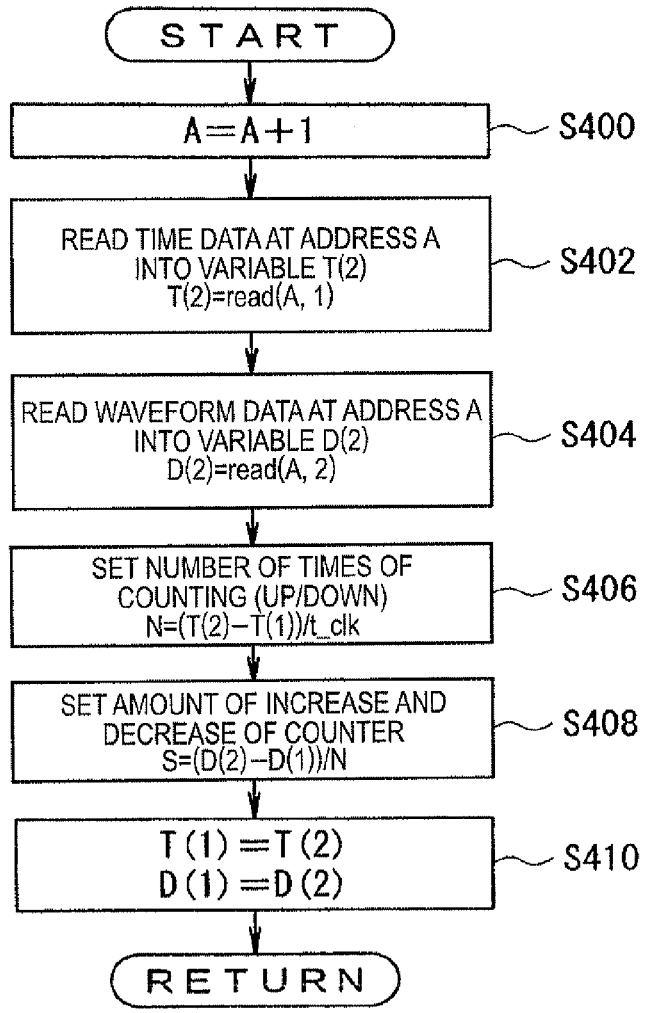
FIG. 13 is a flowchart showing a counter condition setting process corresponding to the steps S308 and S324.
FIG. 14 is a diagram showing an example of waveform information of the third embodiment.

Here, FIG. 13 is a flowchart showing the counter condition setting process corresponding to the steps S308 and S324.

When the process proceeds to the step S308 or the step S324 and the counter condition setting process is started, the process firstly proceeds to the step S400 as shown in FIG. 13.

In the step S400, the interpolation section 31 adds 1 to the value of the data look-up address A, and then the process proceeds to the step S402.

In the step S402, the interpolation section 31 reads the time data at the address A into a variable T(2), and then the process proceeds to the step S404.

Thus, "T(2)=read (A, 1)" is obtained.

In the step S404, the interpolation section 31 reads the waveform data at the address A into a variable D(2), and then the process proceeds to the step S406.

Thus, "D(2)=read (A, 2)" is obtained.

In the step S406, the interpolation section 31 substitutes the value obtained by dividing the value, which is obtained by subtracting the value of the variable T(1) from the value of the variable T(2), by the time (t_clk) of one cycle of the clock signal clk for the variable N as the number of times of counting in the time axis necessary for reaching the next nodal point, and then the process proceeds to the step S408.

In the step S408, the interpolation section 31 subtracts the value of the variable D(1) from the value of the variable D(2), and substitutes the value obtained by dividing the result of the subtraction by the value of the variable N for the variable S as the amount of increase and decrease of the counting in the voltage axis in each counting operation, and then the process proceeds to the step S410.

In the step S410, the interpolation section 31 substitutes the value of the variable T(2) for the variable T(1), and the value of the variable D(2) for the variable D(1), then the series of process is terminated, and the process returns to the original process.

Then, with reference to FIGS. 14 and 15, a specific operation of the fluid jet device 1 of the present embodiment will be explained.

Here, FIG. 14 is a diagram showing an example of the waveform information of the present embodiment. Further, FIG. 15 is a diagram showing an output example of the drive signal of the trapezoidal wave.

Since the determination process of $T_{red}$ and the preliminary determination process of $T_{exp}$ are the same as in the first embodiment described above, the process subsequent to the determination will be explained.

When $T_{red}$ and preliminary $T_{exp}$ are determined, the signal waveform generation section 30b then reads out the waveform information of the trapezoidal wave having one cycle the nearest to the double (e.g., 0.2 [ms]) of $T_{red}$ thus determined from the data storage section 30c (step S110).

Here, in the case in which the time length between the nodal points A and E in the waveform information of the trapezoidal wave thus read out is different from $T_{red}$ thus determined as described above, the time information of the waveform information thus read out is corrected.

Then, the time length between the nodal points C and E in the waveform information of the trapezoidal wave thus read out as described above is corrected so as to be equal to or longer than $T_{exp}$ thus preliminarily determined. In the manner as described above, by correcting the waveform information of a single type of trapezoidal wave, the waveform information of the trapezoidal signal waveform is generated (step S112).

It should be noted that as another method of generating the trapezoidal signal waveform, there can be cited a method of generating the signal waveform by combining the anterior half cycle of one of the waveform information of two types of trapezoidal waves with periods different from each other with the posterior half cycle of the other thereof as in the case of the first embodiment described above. Further, regarding the correction of the time length between the nodal points A and E, similarly to the case described above, there is cited a method of performing the correction by expending the time length between the nodal points C and D as in the second embodiment described above when correcting the time length between the nodal points C and E.

Since the subsequent process (steps S114 through S120, and S128) is substantially the same as in the first embodiment, the process after adjusting $T_{exp}$ in the step S128 will be explained.

After adjusting $T_{exp}$, the signal waveform generation section 30b reads out the waveform information of a trapezoidal wave corresponding to the cycle double of $T_{red}$ thus determined as described above from the data storage section 30c (step S130), and corrects the waveform information thus read out so that the time length between nodal points C and E of the waveform information becomes $T_{exp}$ thus adjusted, thereby generating the waveform information after $T_{exp}$ is adjusted (step S112).

Then, the signal waveform generation section 30b outputs the drive request (step S114) to make the drive signal supply section 30d drive the piezoelectric element 401 with the signal waveform of the waveform information thus generated (step S116).

When the drive signal is supplied to the piezoelectric element 401, the signal waveform generation section 30b measures $P_{gen}$ and $P_{sup}$ (step S118), and determines whether or not the measurement results, $T_{red}$, and $T_{exp}$ thus adjusted satisfy the relationship of the formula 1 described above (step S120).

If the waveform information of one cycle of the signal waveform thus generated satisfies the relationship of the formula 1 described above (the branch of "Yes" in the step S120), the signal waveform generation section 30b stores the waveform information into the data storage section 30c in correspondence with the identification number (step S122).

The operation of the drive signal supply process will hereinafter be explained.

When the user holds down a drive switch (not shown), and the drive signal supply instruction is input to the drive section 30, the operation control section 30a outputs the drive signal supply command to the drive signal supply section 30d.

Meanwhile, when receiving the drive signal supply command, the drive signal supply section 30d proceeds to the waveform information setting process (the branch of "Yes" in the step S200).

Since the drive signal supply command includes designated waveform information including the identification information of the waveform information used as the drive signal, the drive signal supply section 30d sets the waveform information with the identification information corresponding to the designated waveform information as the waveform information used for driving (step S202). Here, it is assumed that the waveform information shown in FIG. 14 is set.

When the waveform information used as the drive signal is set, then the interpolation section 31 sets the start address 101 in the data look-up address A (step S300), and subsequently reads the time data t0 at the address 101 into the variable T(1) (step S302). Thus, "T(1)=t0" is obtained.

Subsequently, the interpolation section 31 reads the waveform data P0 at the address 101 into the variable D(1) (step S304). Thus, "D(1)=P0" is obtained.

Then, the interpolation section 31 sets the value P0 of the variable D(1) in the variable cnt as the initial value of the counter (step S306), and the process proceeds to the counter condition setting process (step S308).

When the counter condition setting process is started, the interpolation section 31 firstly adds 1 to the value of the data look-up address A (step S400). Thus, "A=102" is obtained.

Subsequently, the interpolation section 31 reads the time data t1 at the address 102 into the variable T(2) (step S402), and the waveform data P1 at the address 102 into the variable D(2) (step S404). Thus, "T(2)=t1, D(2)=P1" is obtained.

Then, the interpolation section 31 subtracts the value t0 of the variable T(1) from the value t1 of the variable T(2), calculates the number of times of the counting in the time axis by dividing the result of the subtraction by the time (t_clk) of one cycle of the clock signal clk, and substitutes the calculation result "(t1−t0)/t_clk" for the variable N. Thus, "N=(t1−t0)/t_clk" is obtained.

Subsequently, the interpolation section 31 subtracts the value P0 of the variable D(1) from the value P1 of the variable D(2), calculates the amount of increase and decrease of the counter in the voltage axis by dividing the result of the subtraction by the number of times N of the counting, and substitutes the calculation result "(P1−P0)/N" for the variable S. Thus, "S=(P1−P0)/N" is obtained.

Lastly, the interpolation section 31 substitutes the value t1 of the variable T(2) for the variable T(1), and the value P1 of the variable D(2) for the variable D(1), then the counter condition setting process is terminated, and the process returns to the original process (step S410). Thus, "T(1)=t1," "D(1)=P1" are obtained.

When the counter condition with respect to the counter 33 is set, then the interpolation section 31 waits for the sync signal from the sync signal generation section 30e to be detected, and if the sync signal is detected (the branch of "Yes" in the step S310), the interpolation section 31 initializes the variable k by setting "0" therein, and compares the value "0" of the variable k with the value "(t1−t0)/t_clk" of the variable N to determine whether or not the value of the variable k is smaller than the value of the variable N (step S314).

Then, in the period in which the value of the variable k is smaller than the value of the variable N (the branch of "Yes" in the step S314), the signal waveform with the voltage value determined by the value of the variable cnt is output from the counter 33 to the amplifier 35 in every clock (step S316), then the value of the variable S is added to the value of the variable cnt (step S318), and then 1 is added to the value of the variable k (step S320).

Figure 15:
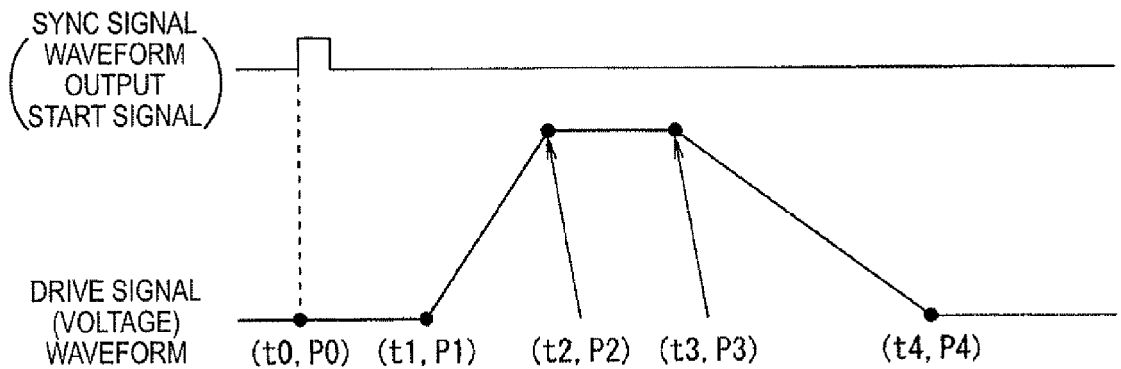
FIG. 15 is a diagram showing an output example of a drive signal of a trapezoidal wave.
Figure 16:
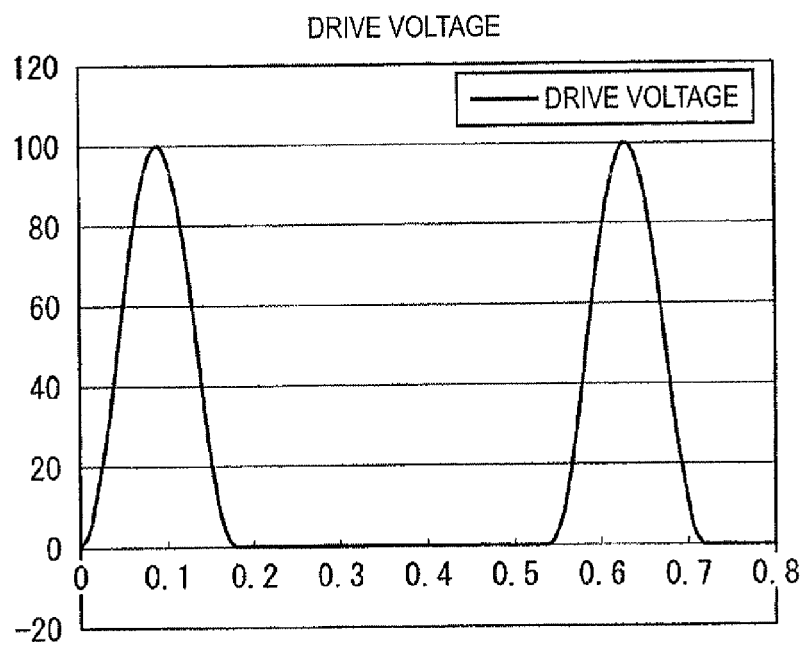
FIG. 16 is a diagram showing an example of a drive signal having a burst wave for driving the piezoelectric element.

Since in the example shown in FIG. 15 P0 and P1 are set to be "0[V]," the amount S of increase and decrease of the counter becomes "0," and therefore, even if the value of the variable k increases, the value of the variable cnt is kept to the initial value of "0." Therefore, the counter 33 keeps outputting the signal waveform of "0[V]" to the amplifier 35 while the value of the variable k is kept smaller than the value of the variable N.

Subsequently, when the value of the variable k exceeds the value of the variable N (the brunch of "No" in the step S314), since the next nodal point data exists here (the branch of "Yes" in the step S322), the process proceeds to the counter condition setting process again (step S324).

Similarly to the above, after executing the process of the steps S400 through S410, "A=103," "T(2)=t2," "D(2)=P2," "N=(t2−t1)/t_clk," "S=(P2−P1)/N," "T(1)=t2," and "D(1)=P2" are obtained.

When the counter condition with respect to the counter 33 is set, then the interpolation section 31 waits for the sync signal from the sync signal generation section 30e to be detected, and if the sync signal is detected (the branch of "Yes" in the step S310), the interpolation section 31 initializes the variable k by setting "0" therein, and compares the value "0" of the variable k with the value "(t2−t1)/t_clk" of the variable N to determine whether or not the value of the variable k is smaller than the value of the variable N (step S314).

Then, in the period in which the value of the variable k is smaller than the value of the variable N (the branch of "Yes" in the step S314), the signal waveform with the voltage value determined by the value of the variable cnt is output from the counter 33 to the amplifier 35 in every clock (step S316), then the value of the variable S is added to the value of the variable cnt (step S318), and further 1 is added to the value of the variable k (step S320).

Since in the example shown in FIG. 15, P2 is set to be a "value (assumed to be 3[V] here) larger than 0[V]," the amount S of increase and decrease of the counter becomes "(3/N)[V]," and the value of the variable cnt increases by "(3/N)[V]" every time the value of the variable k increases by 1. Therefore, the counter 33 outputs the signal waveform, which increases by "(3/N)[V]" every time the value of the variable k increases by "1," to the amplifier 35.

Subsequently, when the value of the variable k exceeds the value of the variable N (the brunch of "No" in the step S314), since the next nodal point data exists here (the branch of "Yes" in the step S322), the process proceeds to the counter condition setting process again (step S324).

Similarly to the above, after executing the process of the steps S400 through S410, "A=104," "T(2)=t3," "D(2)=P3," "N=(t3−t2)/t_clk," "S=(P3−P2)/N," "T(1)=t3," and "D(1)=P3" are obtained.

When the counter condition with respect to the counter 33 is set, then the interpolation section 31 waits for the sync signal from the sync signal generation section 30e to be detected, and if the sync signal is detected (the branch of "Yes" in the step S310), the interpolation section 31 initializes the variable k by setting "0" therein, and compares the value "0" of the variable k with the value "(t3−t2)/t_clk" of the variable N to determine whether or not the value of the variable k is smaller than the value of the variable N (step S314).

Then, in the period in which the value of the variable k is smaller than the value of the variable N (the branch of "Yes" in the step S314), the signal waveform with the voltage value determined by the value of the variable cnt is output from the counter 33 to the amplifier 35 in every clock (step S316), then the value of the variable S is added to the value of the variable cnt (step S318), and further 1 is added to the value of the variable k (step S320).

Since in the example shown in FIG. 15, P3 is set to be "the same value 3[V] as that of P2," the amount S of increase and decrease of the counter becomes "0[V]," and therefore, even if the value of the variable k increases, the value of the variable cnt is kept to "3[V]." Therefore, the counter 33 keeps outputting the signal waveform of "3[V]" to the amplifier 35 while the value of the variable k is kept smaller than the value of the variable N. Therefore, the counter 33 outputs the signal waveform of "3[V]" to the amplifier 35 every time the value of the variable k increases by "1."

Subsequently, when the value of the variable k exceeds the value of the variable N (the brunch of "No" in the step S314), since the next nodal point data exists here (the branch of "Yes" in the step S322), the process proceeds to the counter condition setting process again (step S324).

Similarly to the above, after executing the process of the steps S400 through S410, "A=105," "T(2)=t4," "D(2)=P4," "N=(t4−t3)/t_clk," "S=(P4−P3)/N," "T(1)=t4," and "D(1)=P4" are obtained.

When the counter condition with respect to the counter 33 is set, then the interpolation section 31 waits for the sync signal from the sync signal generation section 30e to be detected, and if the sync signal is detected (the branch of "Yes" in the step S310), the interpolation section 31 initializes the variable k by setting "0" therein, and compares the value "0" of the variable k with the value "(t4−t3)/t_clk" of the variable N to determine whether or not the value of the variable k is smaller than the value of the variable N (step S314).

Then, in the period in which the value of the variable k is smaller than the value of the variable N (the branch of "Yes" in the step S314), the signal waveform with the voltage value determined by the value of the variable cnt is output from the counter 33 to the amplifier 35 in every clock (step S316), then the value of the variable S is added to the value of the variable cnt (step S318), and further 1 is added to the value of the variable k (step S320).

Since in the example shown in FIG. 15, 94 is set to be "0[V]," and P3 is set to be "3[V]," the amount S of increase and decrease of the counter becomes "(−3/N)[V]," and the value of the variable cnt decreases by "(3/N)[V]" from 3[V] every time the value of the variable k increases by 1. Therefore, the counter 33 outputs the signal waveform, which decreases by "(3/N)[V]" from the previous value every time the value of the variable k increases by "1," to the amplifier 35.

Subsequently, when the value of the variable k exceeds the value of the variable N (the branch of "No" in the step S314), since the next nodal point data does not exist here (the branch of "No" in the step S322), the process proceeds to the original process, and if a halt command or a termination command is provided, the drive signal supply process is halted or terminated. On the other hand, if neither the halt command nor the termination command is provided, the process from the step S300 is executed again with respect to the waveform information thus set. Thus, the signal waveform of the same waveform information can continuously be output.

It should be noted that the operation of the fluid jet emitting section 2 after supplying the piezoelectric element 401 with the drive signal is substantially the same as the operation of the first embodiment described above, and therefore, the explanations therefor will be omitted.

As explained hereinabove, if the nodal point data of the trapezoidal wave is stored in the data storage section 30c, the fluid jet device 1 of the present embodiment can supply the piezoelectric element 401 of the pulsation generation section 100 with the drive signal composed of the analog trapezoidal signal waveform while interpolating the data between the nodal points using the nodal point data.

Thus, since the data capacity of the waveform information can significantly be reduced in comparison with the case of the sine waves, the memory device with a large capacity is not required, and the fluid jet device can be configured with relatively low cost.

Further, since it is arranged that the signal waveform output process is executed using the algorithms shown in the flow charts of the steps S208 through S220 described above and the steps S300 through S324 described above, even if the drive signal supply command and the drive signal halt command are input at any timing, it is possible to supply the piezoelectric element 401 with the drive signal so as to always start with the head of the waveform and end with the tail thereof.

Thus, since it does not occur that the drive signal is supplied to the piezoelectric element 401 from the middle of the waveform or that the drive signal is suddenly switched to a no signal state in the middle of the supply of the drive signal, the piezoelectric element 401 can be prevented from being damaged by, for example, suddenly shrinking the piezoelectric element 401.

It should be noted that although in the first embodiment the configuration capable of generating the waveform information with an appropriate signal waveform in accordance with the measurement values of $P_{gen}$ and $P_{sup}$ of the fluid jet emitting section 2 is explained, the configuration is not limited thereto, but can be a configuration of previously generating the waveform information of the signal waveform corresponding to the values of $P_{gen}$ and $P_{sup}$, and holding the waveform information. According to this configuration, although the drive section 30 becomes only available for the fluid jet emitting section 2 of the same pressure specification, since the pressure sensor, the signal waveform generation section 30b, and so on become unnecessary to be provided, the corresponding cost (the cost of the sensor, the cost of writing the program, and so on) can be reduced. Further, as another embodiment, it is also possible to adopt a configuration in which the values of $P_{gen}$ and $P_{sup}$ measured previously prior to the shipment are stored in the fluid jet emitting section 2 (e.g., by adding a memory device storing the values), and the values of $P_{gen}$ and $P_{sup}$ are obtained when replacing the fluid jet emitting section 2 or powering on to generate the waveform information of the signal waveform corresponding to the values of $P_{gen}$ and $P_{sup}$. According to this configuration, since it can cope with a plurality of types of pressure specifications, and need for providing the pressure sensor for measuring $P_{gen}$ and $P_{sup}$ is eliminated, the cost can be reduced accordingly.

Further, although the first through third embodiments described above, which are preferable specific examples of the invention, are provided with various technically preferable limitations, the scope of the invention is not limited to these embodiments unless the description to limit the invention thereto is particularly presented in the explanations described above. Further, the drawings used in the explanations described above are schematic diagrams having contraction scales in the vertical and horizontal directions of the members or parts different from the actual scales for the sake of convenience of illustration.

Further, the invention is not limited to the first through third embodiments described above but includes modifications and improvements within a range where the advantages of the invention can be achieved.

What is claimed is:
1. A fluid jet device comprising:
a fluid chamber with a variable capacity;
an entrance channel communicated with the fluid chamber;
an exit channel communicated with the fluid chamber;
a capacity varying section adapted to vary the capacity of the fluid chamber in response to supply of a drive signal;
an opening section communicated with the exit channel;
a pressure generation section adapted to supply the entrance channel with a fluid; and
a drive signal supply section adapted to supply the capacity varying section with a drive signal including a compressing drive waveform section making the capacity varying section operate so as to compress the capacity of the fluid chamber and a restoring drive waveform section making the capacity varying section operate so as to restore the capacity of the fluid chamber before compressing the capacity in a signal waveform of one cycle; and
a storage section adapted to store waveform information of the drive signal;
wherein the drive signal supply section controls supply content of the drive signal so as to provide a restoring period adapted to restore a steady state of the fluid flowing toward an inside of the fluid chamber in a period from when the compressing drive waveform section in the drive signal is supplied to the capacity varying sec- tion to when a subsequent one of the compressing drive waveform section is supplied to the capacity varying section, and the drive signal supply section generates the drive signal based on the waveform information stored in the storage section, and supplies the capacity varying section with the drive signal.

2. The fluid jet device according to claim 1, wherein
a time length of the compressing drive waveform section is denoted as $T_{red}$,
a time length of the restoring drive waveform section is denoted as $T_{exp}$,
average pressure in the fluid chamber in a supply period of the compressing drive waveform section is denoted as $P_{gen}$,
pressure applied to the entrance channel in the fluid chamber on a pressure generation section side in a supply period of the restoring drive waveform section is denoted as $P_{sup}$, and
the drive signal supply section supplies the capacity varying section with the drive signal configured including the compressing drive waveform section with the time length $T_{red}$ and the restoring drive waveform section with the time length $T_{exp}$ satisfying a relationship of a following formula $$T_{red} \times (P_{gen} - P_{sup}) \leq T_{exp} \times P_{sup}.$$

3. The fluid jet device according to claim 1, wherein
the drive signal supply section controls the supply content of the drive signal so as to provide the restoring period in the supply period of the restoring drive waveform section.

4. The fluid jet device according to claim 3, wherein
the drive signal supply section supplies the capacity varying section with the drive signal having a constant waveform section between the compressing drive waveform section and the restoring drive waveform section, the constant waveform section forming a constant signal level in a part of the restoring drive waveform section, the constant signal level corresponding to the restoring period.

5. The fluid jet device according to claim 1, wherein
the drive signal supply section supplies the capacity varying section with the drive signal having the signal waveform of one cycle configured by combining a part of a sine wave, which forms the compressing drive waveform section, and a time length of one cycle of which is T1, and a part of a sine wave, which forms the restoring drive waveform section, and a time length of one cycle of which is T2 (T1<T2).

6. The fluid jet device according to claim 1, wherein
a shape of a trapezoidal wave is adopted as the signal waveform of one cycle.

7. The fluid jet device according to claim 6, wherein
the storage section stores nodal point information of the trapezoidal wave as the waveform information, and
the drive signal supply section generates the drive signal of the trapezoidal wave based on the nodal point information stored in the storage section.

8. The fluid jet device according to claim 1, wherein
a diameter of an end of the exit channel on a fluid chamber side is set to be larger than a diameter of an end of the exit channel on an opening section side.

9. The fluid jet device according to claim 1, wherein
an inertance of the entrance channel is set to be larger than an inertance of the exit channel.

10. The fluid jet device according to claim 1, wherein
a combined inertance on an upstream side of the fluid chamber including the entrance channel is larger than an inertance on a down stream side of the fluid chamber including the exit channel.

11. The fluid jet device according to claim 1, further comprising:
a connection channel having a first end communicated with the exit channel, and a second end provided with the opening section having a diameter smaller than a diameter of the exit channel; and
a connection channel tube through which the connection channel penetrates, and which transmits pulsation of the fluid flowing from the fluid chamber to the opening section.

12. The fluid jet device according to claim 1, wherein
the capacity varying section includes:
a diaphragm adapted to seal an end of the fluid chamber, and
a piezoelectric element having one end fixed to the diaphragm and one of expanding and shrinking in a direction perpendicular to a seal surface in response to supply of the drive signal, and
the drive signal supply section makes the piezoelectric element expand to deform the diaphragm toward an inside of the fluid chamber by supplying the compressing drive waveform section in the drive signal, and makes the piezoelectric element shrink to restore the diaphragm in a deformed state to the diaphragm in a state prior to the deformation by supplying the restoring drive waveform section in the drive signal.

13. A surgical instrument adapted to assist a therapeutic treatment of an affected area by fluid jet emission, comprising:
the fluid jet device according to claim 1.

14. A method of driving a fluid jet device comprising:
(a) providing a fluid chamber with a variable capacity, an entrance channel and an exit channel each communicated with the fluid chamber, a capacity varying section adapted to vary a capacity of the fluid chamber in response to supply of a drive signal, an opening section communicated with the exit channel, a pressure generation section adapted to supply the entrance channel with a fluid, and a drive signal supply section; and
(b) making the drive signal supply section supply the capacity varying section with a drive signal including a compressing drive waveform section making the capacity varying section operate so as to compress the capacity of the fluid chamber and a restoring drive waveform section making the capacity varying section operate so as to restore the capacity of the fluid chamber before compressing the capacity in a signal waveform of one cycle,
wherein in step (b), the drive signal supply section is made to control supply content of the drive signal so as to provide a restoring period adapted to restore a steady state of the fluid flowing toward an inside of the fluid chamber in a period from when the compressing drive waveform section in the drive signal is supplied to the capacity varying section to when a subsequent one of the compressing drive waveform section is supplied to the capacity varying section.

* * * * *